US005792217A

United States Patent [19]

Camps et al.

[11] Patent Number: 5,792,217
[45] Date of Patent: Aug. 11, 1998

[54] TEMPORARY BIPOLAR HEART WIRE

[75] Inventors: Antoine N. J. M. Camps, Wittem, Netherlands; Farid Moumane, Trelon, France; Gerrit Frederik Landheer, Galeen, Netherlands; Frank L. Skubitz, Andover, Minn.

[73] Assignee: Medtronic, Inc., Minneapolis, Minn.

[21] Appl. No.: 672,722

[22] Filed: Jun. 28, 1996

[51] Int. Cl.$^6$ ...................................................... A01N 1/04
[52] U.S. Cl. .......................... 607/119; 607/119; 607/132; 600/372; 600/373; 600/374; 600/375
[58] Field of Search .................................. 607/116, 119, 607/126, 127, 128, 132; 128/642

[56] References Cited

U.S. PATENT DOCUMENTS

| | | |
|---|---|---|
| 3,035,583 | 6/1962 | Hirsch et al. . |
| 3,125,095 | 3/1964 | Kaufman et al. . |
| 3,244,174 | 4/1966 | Wesbey et al. . |
| 3,949,756 | 4/1976 | Ace . |
| 4,010,756 | 3/1977 | DuMont et al. . |
| 4,054,144 | 10/1977 | Hoffman et al. . |
| 4,338,947 | 7/1982 | Williams . |
| 4,341,226 | 7/1982 | Peters . |
| 4,442,840 | 4/1984 | Wojciechowicz . |
| 4,444,207 | 4/1984 | Robicsek . |
| 4,530,368 | 7/1985 | Saulson et al. . |
| 4,541,440 | 9/1985 | Parsonnet . |
| 4,553,554 | 11/1985 | Lemole . |
| 4,630,617 | 12/1986 | Ritter et al. . |
| 4,633,880 | 1/1987 | Osypka et al. . |
| 4,693,258 | 9/1987 | Osypka et al. . |
| 4,972,833 | 11/1990 | Wildon . |
| 5,217,027 | 6/1993 | Hermens . |
| 5,241,957 | 9/1993 | Camps et al. . |
| 5,314,463 | 5/1994 | Camps et al. . |
| 5,324,323 | 6/1994 | Bui .................................... 607/132 |
| 5,350,419 | 9/1994 | Bendel et al. . |
| 5,423,876 | 6/1995 | Camps et al. . |

OTHER PUBLICATIONS

"Using the Medtronic®Model 5805 Temporary Bipolar Lead," Dec. 1975.
"Technical Manual Sales Brochure," Medtronic, Inc., Dec. 1994.
Medtronic's Solutions to Temporary Pacing Problems Sales Brochure.

*Primary Examiner*—John P. Lacyk
*Assistant Examiner*—David Ruddy
*Attorney, Agent, or Firm*—Thomas F. Woods; Harold R. Patton

[57] ABSTRACT

The present invention includes within its scope a temporary lead for pacing, sensing, monitoring, or defibrillating at least a portion of a human or animal organ, and methods for implanting and making same. The lead has at least two electrodes and distal and proximal ends, and a novel weakened zone disposed between the blunt end of a needle and at least two electrical connectors attached to the proximal end of the lead body. The novel weakened zone permits the needle to be separated from the connectors by application of a sufficiently large bending moment or pulling force thereto. Following separation of the connectors from the needle, the connectors may be attached directly and quickly to an external electrical apparatus.

149 Claims, 14 Drawing Sheets

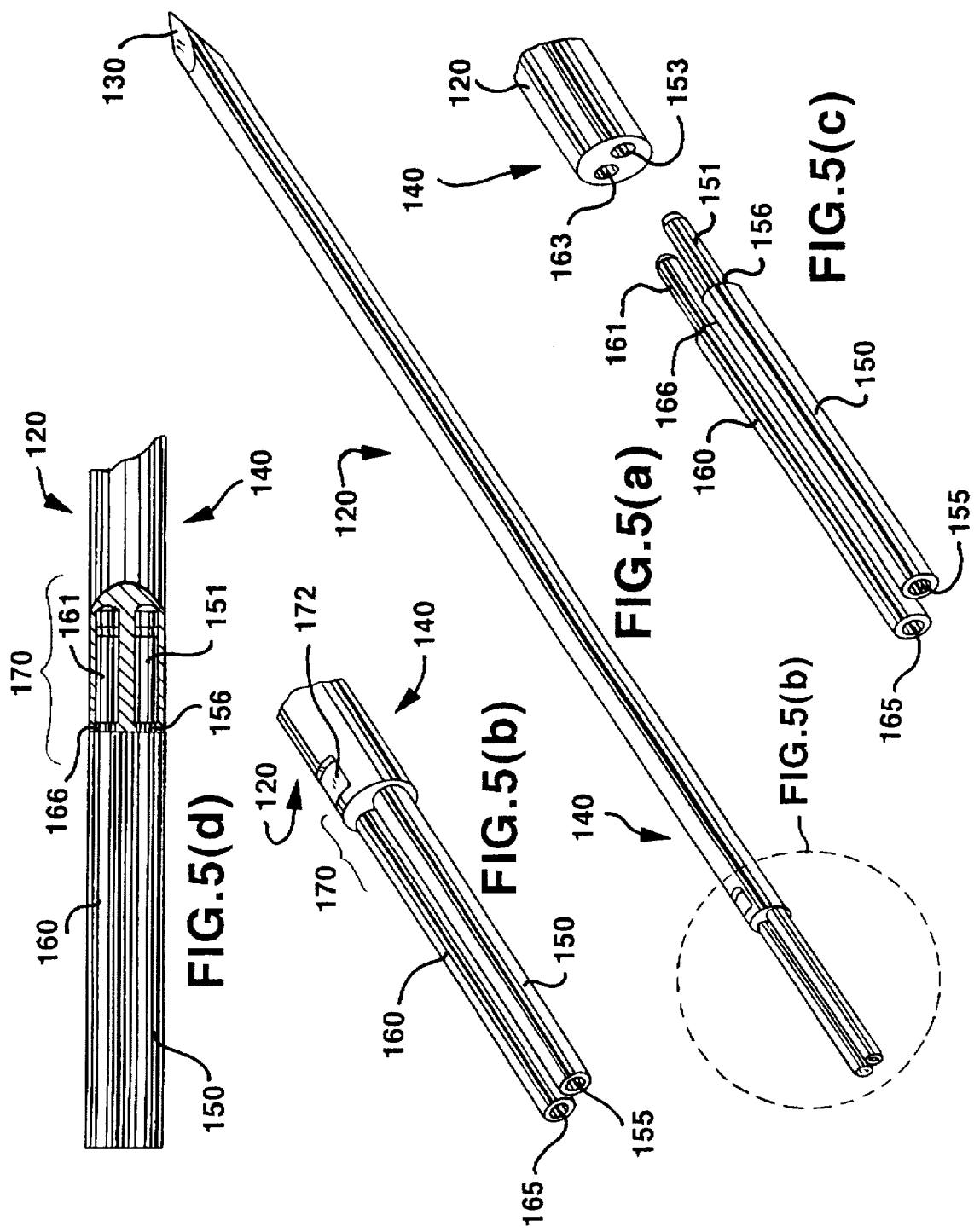

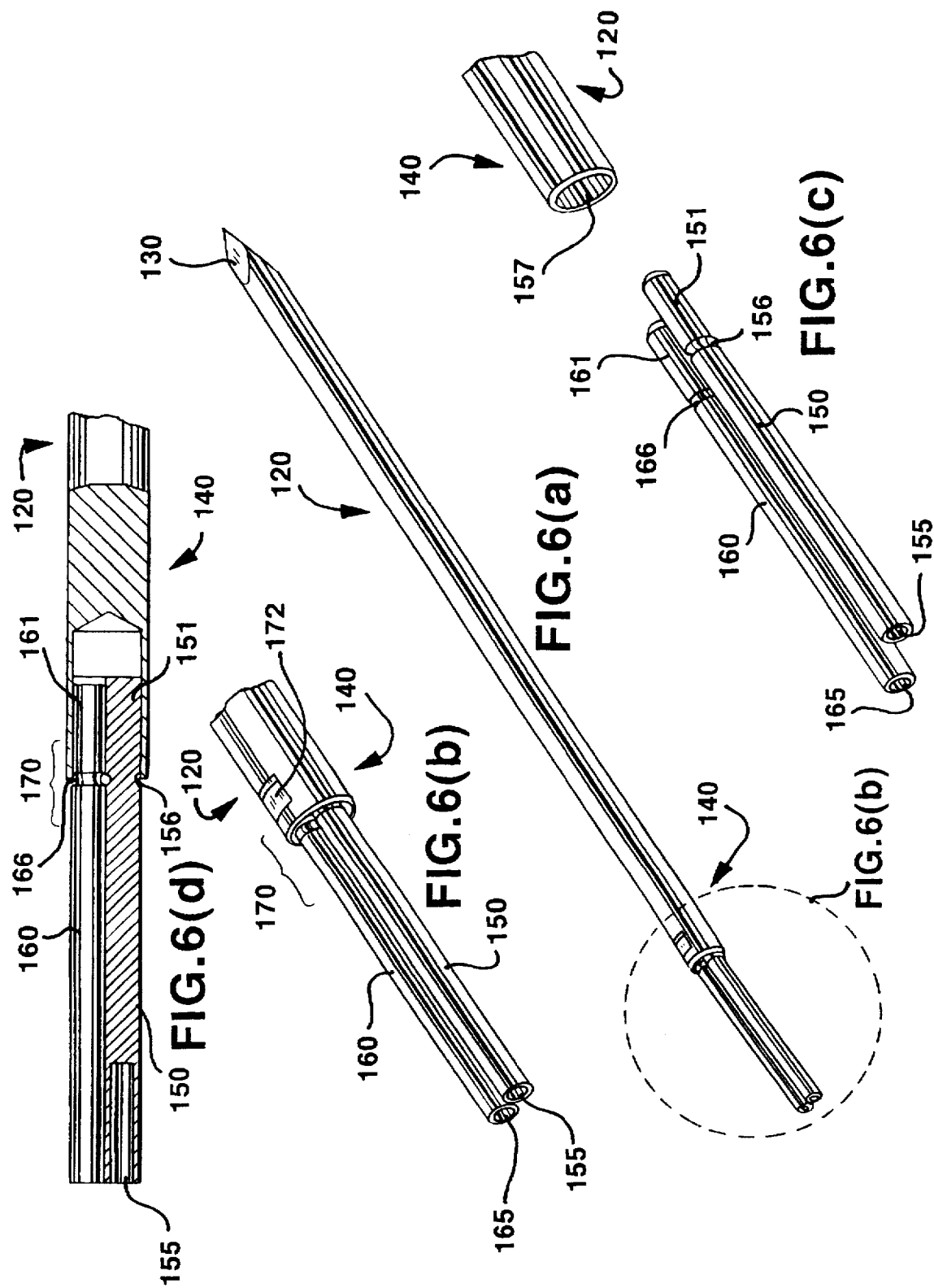

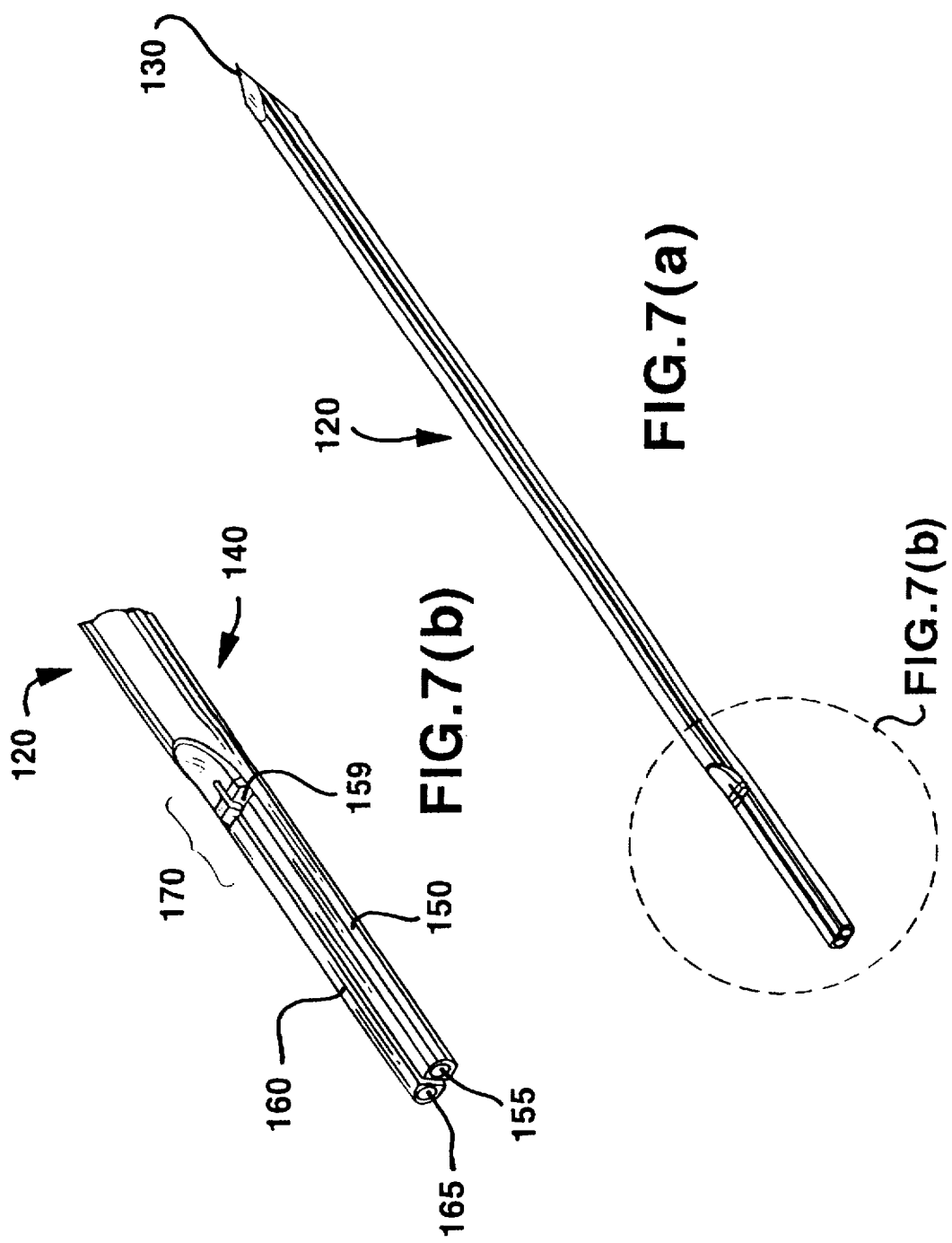

TEMPORARY BIPOLAR HEART WIRE

FIELD OF THE INVENTION

The present invention relates generally to heart wires and leads, and more particularly to temporary bipolar heart wires and leads for pacing, defibrillating and monitoring.

BACKGROUND OF THE INVENTION

Unipolar and bipolar surgically implanted temporary heart wires are well known in the art, some examples of which may be found in the issued U.S. Patents listed in Table 1 below.

TABLE 1

Prior Art Patents

| U.S Pat. No. | Title |
| --- | --- |
| 3,035,583 | Conductive Sutures |
| 3,125,095 | Flexible Stainless Steel Sutures |
| 3,664,347 | Electric Heart Stimulation Method and Electrode |
| 3,949,756 | Sutures with Notch Near Needle-Suture Junction |
| 4,010,756 | Heart Pacer Lead Wire with Break-Away Needle |
| B1 4,010,756 | Heart Pacer Lead Wire with Break-Away Needle |
| 4,054,144 | Short-Crimp Surgical Needle |
| 4,338,947 | Positive Fixation Heart Wire |
| 4,341,226 | Temporary Lead with Insertion Tool |
| 4,442,840 | Electrical Connector Apparatus and Method for a Temporary Cardiac Pacing Wire |
| 4,444,207 | Method of Anchoring a Temporary Cardiac Pacing Lead |
| 4,530,368 | Temporary Bipolar Pacing Lead |
| 4,541,440 | Bipolar Epicardial Temporary Pacing Lead |
| 4,553,554 | Electrical Lead and Method for Temporary Cardiac Pacing |
| 4,630,617 | Heart Pacer Lead Wire with Pull-Away Needle |
| 4,633,880 | Surgical Electrode |
| 4,693,258 | Surgical Electrode for Cardiac Pacing and Monitoring |
| 4,972,833 | Epicardiac Pacing Lead |
| 5,217,027 | Temporary Cardiac Lead |
| 5,241,957 | Bipolar Temporary Pacing Lead and Connector and Permanent Bipolar Nerve Wire |
| 5,314,463 | Bipolar Nerve Electrode |
| 5,350,419 | Cardiac Pacing Lead |
| 5,423,876 | Intramuscular Lead Having Improved Insertion |

All patents listed in Table 1 hereinabove are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

Surgically implanted temporary heart wires for use as heart pacer and monitoring electrodes are well known in the medical profession. In general, such a heart wire is constructed of a number of fine, stainless steel wires twisted together to form a single, flexible, multifilament electrode wire. The major portion of the wire is typically insulated with a polyethylene, polytetrafluoroethylene, silicone, nylon, or other suitable electrically nonconductive and biocompatible materials, with a short length of wire at either end left uninsulated.

To one uninsulated end of such an electrode wire there is generally attached by swaging or other means a fine curved needle for piercing the heart tissue to place the uninsulated end of the electrode in the myocardium or epicardium. At the other end of such an electrode wire there is generally affixed a Keith-type cutting needle for piercing the thoracic wall to lead the electrode to an outer point for connection with the pacemaker. Once the electrode has been properly positioned, the curved needle and the Keith-type needle are typically clipped off and the uninsulated end of the electrode is ready for attachment to a pacemaker or monitoring device.

Some prior art unipolar heart wires have break-away Keith-type needles attached to their proximal ends, where no clipping is required to remove the needle from the heart wire. Other prior-art Keith-type break-away needles require the use of, or most preferably employ, an external adapter or transition box for breaking the needle in the appropriate location and facilitating attachment of electrical conductors in the lead to an external electrical apparatus. See, for example, the bipolar heart wire and corresponding external connector disclosed in U.S. Pat. No. 5,241,957, where the external connector is required to establish electrical connection between an EPG or PSA and the heart wire.

Many known heart wires are characterized in having one of the two following disadvantages. First, when some known unipolar heart wires are used in applications requiring two electrodes, two different, separate heart wires must be attached to the heart in two separate procedures. Attaching two such heart wires consumes valuable time at a critical stage in heart surgery. Second, when some known bipolar heart wires are used, the needle attached to the proximal end of the heart wire for piercing the transthoracic wall must be clipped off with a scissors or other tool, and pin connectors must be attached to the resulting bare separate wires for establishing electrical connection to an external pacemaker or external electrical apparatus. These steps of needle removal and wire attachment are separate, time consuming acts, and also occur at a critical stage in heart surgery. Moreover, upon repeated attachment, removal and reattachment, the ends of the stainless steel wire may fray and become difficult to work with.

What is needed is a heart wire that attaches easily and quickly to the heart but which also has convenient, easy-to-use connectors disposed between the proximal end of the heart wire and an external pulse generator (EPG), pacing system analyzer (PSA), defibrillator or other such external electrical apparatus. Most preferably, the heart wire should not require substantial electrical or mechanical manipulations by the surgeon, should be comfortable to the patient, and should establish secure and reliable electrical contacts. Finally, the heart wire should be reasonably economical to manufacture.

SUMMARY OF THE INVENTION

The present invention has certain objects. That is, the present invention provides solutions to problems existing in the prior art. It is an object of the present invention to provide a surgical electrode having a needle, the sharpened proximal end of which can be removed without cutting. It is a further object of this invention to provide a surgical electrode which is quickly and easily attached to an external electrical apparatus after the sharpened end of the needle has been removed. It is yet a further object of this invention to provide surgical electrodes having electrical connecting means adapted for specific electrical devices.

The present invention has certain advantages. More particularly, the heart wire of the present invention: (a)

reduces patient trauma; (b) reduces the number of puncture sites in the myocardium or epicardium; (c) reduces the number of puncture sites in the thorax; (d) is easy to use; (e) permits two electrodes to be implanted quickly during a critical stage of heart surgery; (f) has electrodes spaced a predetermined optimal distance apart for sensing and pacing applications; (g) attaches to external pacemakers, defibrillators, monitoring equipment and other external electrical apparatus quickly, easily, securely and reliably; (h) does not require lead wires to be clipped with scissors; (i) requires no use of an external, separate adapter or transition box for separating or breaking the needle from the connectors; (j) requires no use of an external, separate adapter or transition box for establishing electrical connection between the electrodes and an external electrical apparatus; (k) prevents the distal ends of electrode wires from becoming frayed; (l) has fewer parts than many prior art heart needles; (m) is less expensive to manufacture; (n) helps reduce health care costs, and (o) increases patient safety owing to shortened implantation times and quicker connection to external pacing, defibrillating or monitoring equipment.

The heart wire and needle of the present invention have certain features, including one or more of the following: (a) a chest needle having a pointed or proximal end and a blunt or distal end, the blunt end being breakingly, snappingly, crimpingly, compressionally, slidingly, elastically, gluingly, viscously, vacuumingly or otherwise attached separably to the proximal ends of at least two connectors; (b) at least two connectors that upon being separated from the blunt end of the needle form pins or other structures suitable for fitting in or otherwise appropriately engaging an external connector configured to receive the connectors, where the external connector is attached to an external electrical apparatus for monitoring, pacing or defibrillating the heart; (c) a curved, straight or otherwise shaped needle disposed at the distal end of the heart wire that is suitable for piercing the myocardium or epicardium, and (d) two or more electrodes located between the distal and proximal ends of the heart wire for pacing, defibrillating or monitoring the heart.

In one preferred embodiment, the present invention is a temporary bipolar lead having a proximal and a distal end, and comprises a chest needle at its proximal end, the needle having a proximal pointed end and a distal blunt end attached to at least two connectors by a weakened zone, at least two pacing, sensing or defibrillating electrodes disposed near the distal end, a coil affixation member, and a curved needle, the curved needle being attached to the distal end of the lead, the coil affixation member being disposed between the distal end and the proximal end. At least two electrical conductors extend between the electrodes and the connectors.

Other objects, features, advantages and embodiments of the present invention will become apparent upon reading the detailed description and the claims.

BRIEF DESCRIPTION OF THE DRAWINGS

FIG. 5(a) shows a perspective view of a first preferred embodiment of the chest needle of the present invention;

FIG. 5(b) shows an enlarged view of the distal end of the chest needle of FIG. 5(a);

FIG. 5(c) shows an enlarged view of the connectors of FIG. 5(a) prior to the distal ends thereof being inserted in the blunt end of the needle;

FIG. 5(d) shows an enlarged cross-sectional view of the weakened zone of the chest needle of FIG. 5(a);

FIG. 6(a) shows a perspective view of a second preferred embodiment of the chest needle of the present invention;

FIG. 6(b) shows an enlarged view of the distal end of the chest needle of FIG. 6(a);

FIG. 6(c) shows an enlarged view of the connectors of FIG. 6(a) prior to the distal ends thereof being inserted in the blunt end of the needle;

FIG. 6(d) shows an enlarged cross-sectional view of the weakened zone of the Nest needle of FIG. 6(a);

FIG. 7(a) shows a perspective view of a third preferred embodiment of the chest needle of the present invention;

FIG. 7(b) shows an enlarged view of the distal end of the chest needle of FIG. 7(a);

DETAILED DESCRIPTION OF THE PREFERRED EMBODIMENTS

In the figures and the detailed description, like numbers refer to like elements, components and parts throughout.

As used in the specification and claims hereof, the following terms have the particular meanings and definitions set forth below.

The terms "temporary heart wire," "temporary heart lead" and any substantially similar variants thereof mean a temporary heart lead or wire introduced surgically through the myocardium or epicardium from the exterior of the heart, where the lead or wire has at least one electrode near its distal end for monitoring, pacing or defibrillating the heart at or near a myocardial or epicardial site, and where the lead or wire has at least one connector or needle near its proximal end for electrical connection to an external pacing, monitoring, or defibrillating apparatus." The terms "heart wire," "heart lead" and any substantially similar variants thereof are synonymous.

The term "proximal" means that portion of an apparatus, or component or element of an apparatus, disposed in closer proximity to the end of the wire remaining outside a patient's body following the lead implantation procedure than it is to the end of the wire implanted in or attached to the heart.

The term "distal" means that portion of an apparatus, or component or element of an apparatus, disposed in closer proximity to the end of the wire that is inserted through or attached first to the myocardium or epicardium during a wire implantation procedure than it is to the end of the wire that remains outside the patient's body following the lead implantation procedure. The term "chest needle" or "needle" means the proximal end of the heart wire of the present invention, and includes the pointed end of the needle, and the shank and body thereof, or may mean the needle disposed at the distal end of the lead of the present invention, a piercing means, or a means for piercing, depending on the particular context in which the term "needle," "piercing means," or "means for piercing" appears. Additionally, needle 120 may include the weakened zone of the needle intermediate between the blunt end of the needle and the connectors, and may also include the connectors attached to the weakened zone or the blunt end.

The term "blunt" means the shank of the needle and that portion of the chest needle disposed proximally of the connectors and in proximity thereto. The blunt portion of the needle may include further that portion of the needle connected directly to the proximal ends of the connectors.

Figure 1:
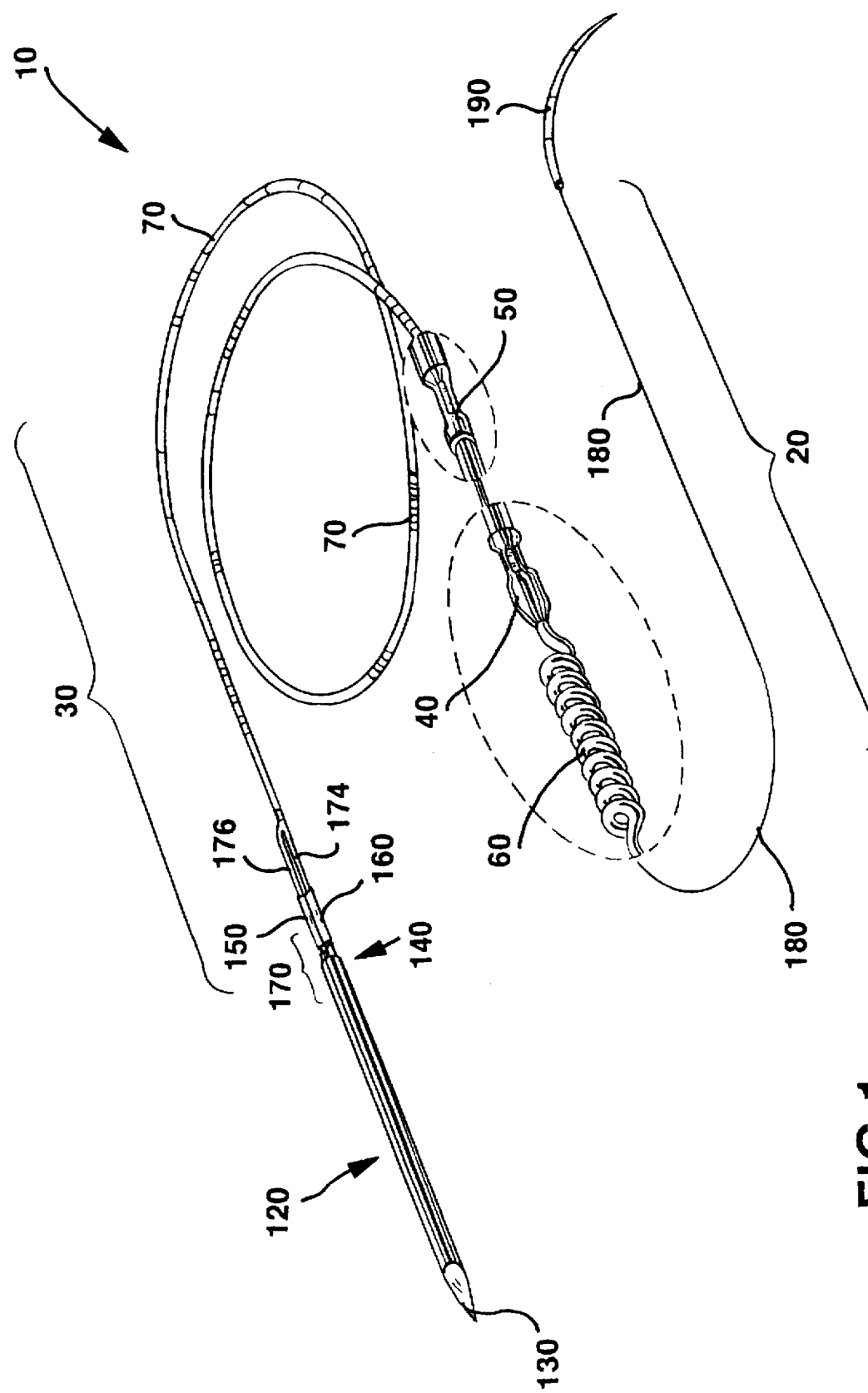
FIG. 1 shows a perspective view of a preferred embodiment of the present invention.

FIG. 1 shows a perspective view of a preferred embodiment of the present invention designed specifically for pacing and sensing applications. Heart lead or wire 10 has distal end 20 and proximal end 30, and most preferably comprises needle 120, connectors 150 and 160, weakened zone 170, coaxial conductor or lead body 70, proximal electrode 50, distal electrode 40, coil affixation member 60, strand 180 and curved atraumatic needle 190.

Strand 180, preferably formed of polypropylene and constituting a monofilament, forms coil affixation member 60, attaches to distal electrode 40 and extends to atraumatic curved needle 190. Coil affixation member 60 may be similar to the type of coil disclosed in U.S. Pat. No. 4,341,226. Coil 60 ensures secure temporary fixation of wire 10 in the heart and prevents dislodgments which might otherwise occur were a smooth tipped lead employed. Most preferably, one length of polypropylene comprises coil 60 and strand 180. More than one curved needle 190 may be attached to distal end 20 of lead 10. For example, each conductor of lead body 70 may terminate in a separate curved needle.

Lead body 70 may comprise any pair of suitable flexible electrical conductors, such as coaxial conductors or so-called "lamp cord" or "zip-cord" (e.g., side-by-side) conductors. Most preferably, lead body 70 is a coaxial pair of inner and outer electrical conductors, where the conductors are formed of helically wound strands of multifilament or twisted stainless steel. Lead body 70 most preferably comprises conductors that provide a high degree of flexibility and superior mechanical and electrical properties.

Electrodes 40 and 50 are preferably formed of medical grade stainless steel suitable for temporary applications, and are preferably spaced a predetermined distance apart known to optimize the delivery of pacing pulses or the detection and sensing of cardiac electrical signals. Distal electrode 40 is mechanically and electrically connected by inner conductor 80 (not shown in FIG. 1 but shown in FIGS. 9, 11 and 12) to first connector 150 at the proximal end of lead 10, which, in turn, is mechanically connected to blunt end 140 of needle 120 by weakened zone 170. Proximal electrode 50 is mechanically and electrically connected by outer conductor 90 (not shown in FIG. 1 but shown in FIGS. 9, 11 and 12) to second connector 160 at the proximal end of lead 10, which is also, in turn, mechanically connected to blunt end 140 of needle 120 by weakened zone 170.

Needle 120, most preferably of the atraumatic type, is a chest needle for piercing the thorax, and has pointed end 130 and blunt end 140. Needle 120 is preferably substantially straight between pointed end 130 and blunt end 140. Pointed end 130 has a cutting edge designed for piercing the thoracic wall of the patient. Blunt end 140 attaches breakingly, snappingly, crimpingly, compressionally, adhesively, gluingly, elastically, slidingly or in otherwise suitable connecting yet separable fashion to the proximal ends of connectors 150 and 160. Weakened or pull-apart zone 170 separates the proximal ends of connectors 150 and 160 from blunt end 140. Connectors 150 and 160 most preferably form cylindrically shaped pin connectors having circular cross-sections upon being separated from blunt end 140. Other structural configurations of connectors 150 and 160 fall within the scope of the present invention and include, but are not limited to, pin-shaped connectors having rectangular or square cross-sections, reed-shaped connectors, and flexible connectors.

Lead 10 includes curved needle 190 for piercing the myocardium or epicardium preparatory to drawing the heart wire 10 and its electrodes within the myocardium or epicardium. The proximal end of curved needle 190 is connected to strand 180.

Figure 2:
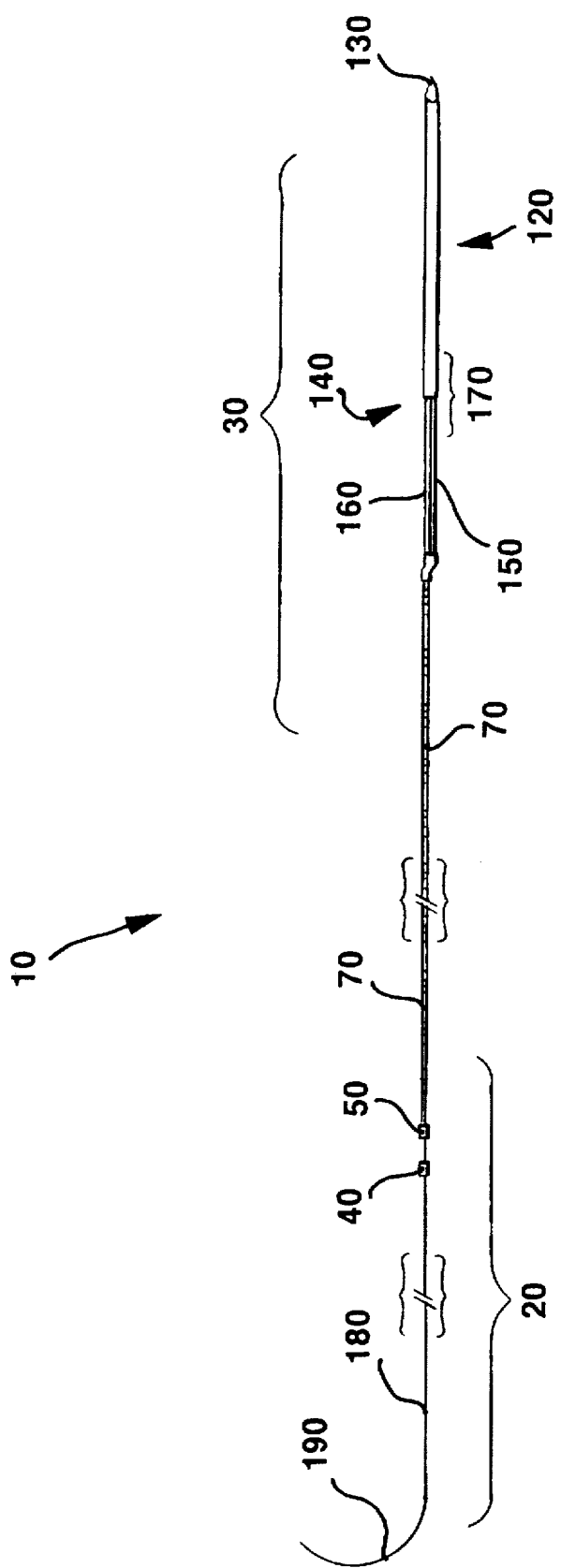
FIG. 2 shows a side view of the lead of FIG. 1.

FIG. 2 shows a side view of the lead of FIG. 1. Note that coil 60 is shown in FIG. 1, but is not shown in FIG. 2. Coil 60 is an optional component of the present invention, and is not required for the practice thereof. For example, the distal end of lead 10 may be secured to the myocardium or epicardium with sutures instead of coil 60.

Figure 3:
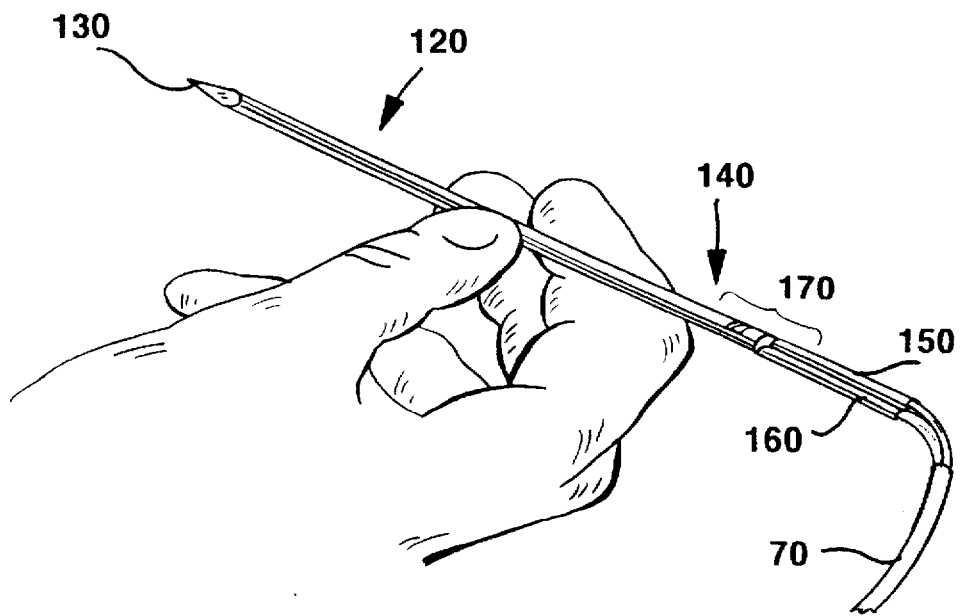
FIG. 3 shows a perspective view of the proximal end of a preferred embodiment present invention.

FIG. 3 shows a perspective view of the proximal end of a preferred embodiment of lead 10. After the surgeon attaches the distal end of lead 10 to the myocardium or epicardium using curved needle 190 and some means for securing the electrodes thereto such as coil 60, needle 120 pierces the patient's thorax and is brought outside the patient's chest.

Figure 4:
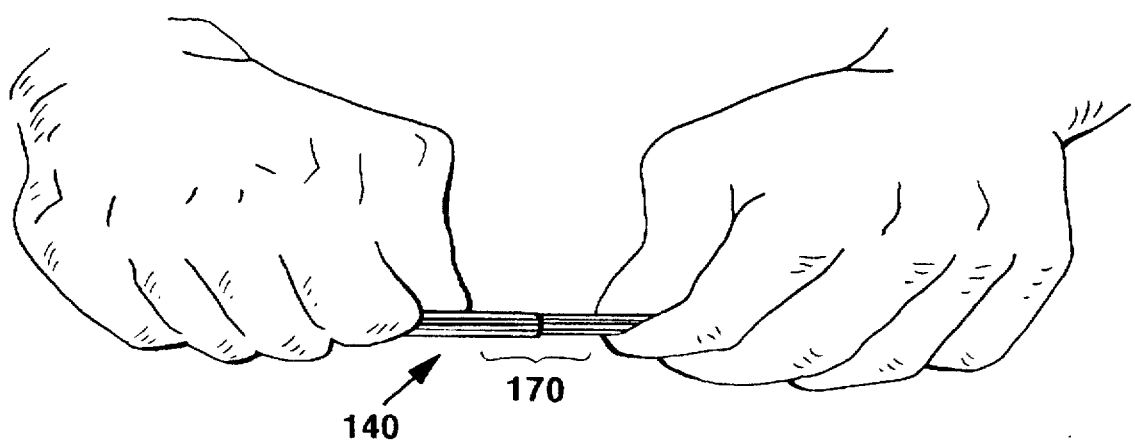
FIG. 4 shows a perspective view of a preferred method of manually applying force to a preferred embodiment of the present invention to cause the connectors to seperate from the blunt end.
Figure 7C:
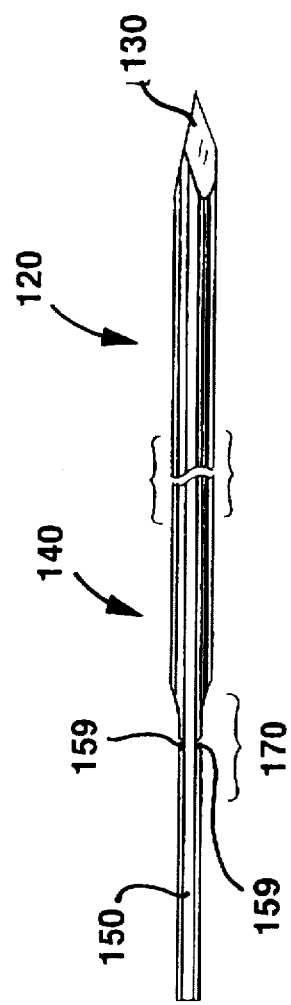
FIG. 7(c) shows a side view of the chest needle of FIG. 7(a)
Figure 7D:
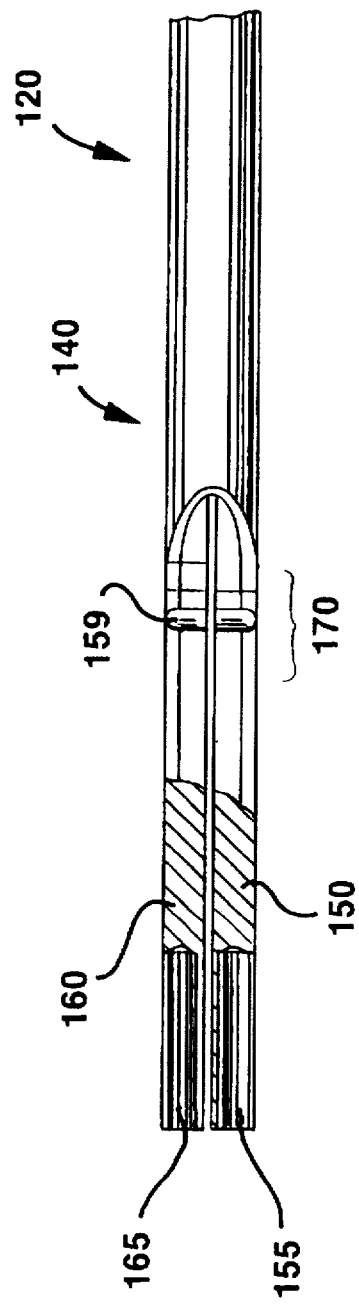
FIG. 7(d) shows an enlarged cross-sectional view of the weakened zone of the chest needle of FIG. 7(a)

When the electrodes have been positioned suitably in the myocardium or epicardium and lead 10 is ready for attachment to an external electrical apparatus such as an EPG, needle 120 is snapped at weakened zone 170 as shown in FIG. 4 by applying a bending moment about zone 170. FIG. 4 shows a perspective view of a preferred method of applying force manually to a preferred embodiment of lead 10 to cause the weakened zone to fail structurally, and to thereby separate the connectors 150 and 160 from blunt end 140. The snapped off portion of the needle is discarded while connectors 150 and 160 are readily inserted into a properly sized receptacle in the EPG or other external electrical apparatus. Connectors 150 and 160 are structures having standardized dimensions, and are configured to permit attachment, removal, and reattachment to an external electrical apparatus in quick, ready, reliable, secure and safe fashion as required, and without encountering frayed ends characteristic of bare, multifilament stainless steel wires.

The present invention permits reliable and secure electrical connections to be established securely, reliably, quickly and safely between at least two electrodes and the external electrical apparatus without the use of a separate connector housing such as that disclosed in U.S. Pat. No. 5,241,947. A separate connector housing adds extra cost to heart wire system. A separate connector housing also increases the likelihood of electrical connection failures occurring between lead 10 and the external electrical apparatus to which lead 10 is connected because the housing contains additional electrical junctions and points of connection not present in the invention. Additionally, a housing like that disclosed in the foregoing '947 patent increases the complexity of, and time required to complete, a heart wire implant procedure. Thus, the present invention may simplify implant procedures, reduce the amount of time required to complete such procedures, and increase the reliability and safety of the heart wire system respecting prior art heart wire systems.

FIGS. 5(a) through 5(d) show different views of a first preferred embodiment of chest needle 120 of the present invention. Reduced diameter pins 151 and 161 are integral to electrically conductive, stainless steel, cylindrically-shaped pin connectors 150 and 160, and extend from the proximal ends thereof. Regions 156 and 166 are scored mechanically, and are disposed between pins 151 and 161 and the proximal ends of connectors 150 and 160. Scoring provides the user with a means of visually identifying the region where the connectors will break. After pins 151 and 161 are fitted into corresponding recesses 153 and 163 disposed within blunt end 140, pins 151 and 161 are swaged or preferably crimped in place by at least one crimp 172, and more preferably by two crimps disposed on opposing sides of needle 120.

The proximal ends of conductors 80 and 90 (not shown in FIGS. 5(a) through 5(d)) slide within recesses 155 and 165 and are crimped in place, thus establishing electrical and mechanical connections between the conductors and the connectors.

Weakened zone 170 preferably comprises the proximal ends of connectors 150 and 160, scored regions 156 and 166, blunt end 140, pins 151 and 161 and recesses 153 and 163. Connectors 150 and 160 separate from needle 120 at scored regions 156 and 166 when a bending moment is applied to weakened zone 170.

Weakened zone 170 may be formed by methods other than scoring. For example, zone 170 may be formed by machining, forming a groove by rotating the connectors or needle in contact with a cutting wheel, or by cutting a notch or forming a crimp on one or both sides of the connectors or the needle. A groove machined or scored in connectors 150 and 160 or pins 151 and 161 reduces the diameter of needle 120 and therefore reduces the strength of needle 120 in weakened zone 170.

Weakened zone 170 may be formed in ways that do not require connectors 150 and 160 to break in certain regions. For example, the amount of force applied when forming crimp 172 may be adjusted so that connectors 150 and 160 may be pulled out of blunt end 140 manually or when a special removal tool is used. Alternatively, pins 151 and 161 may have diameters sized to frictionally engage the inner sidewalls of recesses 155 and 165 with sufficient force to prevent their removal therefrom until a predetermined amount of outward force is applied to pull connectors 150 and 160 from blunt end 140.

Less preferably, weakened zone 170 may be formed by gluing or binding pins 151 and 161 in recesses 153 and 163 using a suitable biocompatible adhesive or viscous material so that a user may pull connectors 150 and 160 out of blunt end 140 when a sufficiently large predetermined force is applied thereto.

Weakened zone 170 may also be obtained by modification of crystalline structure through heat treating by drawing the needle to create a necked down segment, annealing weakened zone 170, or by any other convenient or suitable means.

Grooved or otherwise weakened zone 170 of needle 120 may be located at any convenient distance from blunt end 140. The lengths of the connectors remaining after the pointed end is snapped off should be sufficient for grasping and inserting the connectors into an electrical receptacle. In general, weakened zone 170 is preferably at least 1 centimeter from the distal ends of the connectors or the pointed end 130 of needle 120. Most preferably this distance is between about 2 and 3 centimeters. When the distance between weakened zone 170 and pointed end 130 is less than about 1 centimeter, it becomes difficult to grasp needle 120 for breaking. When connectors 150 and 160 are less than 1 centimeter long, it becomes difficult to handle and insert the connectors into electrical receptacles.

Needle 120 may be curved, straight, or of any other desired, suitable configuration. Pointed end 130 may have any desired cross-sectional configuration. While a triangular cross-section is generally preferred, pointed end 130 may also be circular, triangular, rectangular, square or any other suitable shape in cross-section. Connectors 150 and 160 may also be circular, triangular, rectangular, square or any other suitable shape in cross-section. Such connector cross-sections may find particular use where the connectors are intended to be connected to a particular external electrical apparatus and no other.

Since connectors 150 and 160 establish electrical connection with an external electrical apparatus, insulation 100 and 110 (not shown in FIGS. 5(a) through 5(d)) may extend up to or even over the distal ends of connectors 150 and 160. Abutting the insulation to a location near blunt end 140 and heat shrinking and sealing the joint may provide the advantage of a smooth, continuous and sealed exterior surface that facilitates threading needle 120 through the thoracic wall. In some connectors of the prior art, it has been necessary to provide a segment of uninsulated wire or connector adjacent the needle to allow for electrical connection to an external electrical apparatus after the needle has been clipped off the wire, or to take an extra step of stripping insulation from the wire to provide an electrical connection.

FIGS. 6(a) through 6(d) show different views of a second preferred embodiment of the chest needle of the present invention. Pins 151 and 161 are integral to electrically conductive, stainless steel, cylindrically-shaped pin connectors 150 and 160, and extend from the proximal ends thereof. Regions 156 and 166 are scored mechanically. Blunt end 140 is preferably compressed slightly in the vicinity of axial recess 157 and in a vertical direction to increase the horizontal dimension of axial recess 157 to ease the insertion of pins 151 and 161 therein. Following insertion of pins 151 and 161 in recess 157, blunt end 140 is crimped to form at least one crimp 172, and more preferably two crimps disposed on opposing sides of needle 120.

The proximal ends of conductors 80 and 90 (not shown in FIGS. 6(a) through 6(d)) slide within recesses 155 and 165 and are crimped in place at crimps 154 and 164 (shown in FIG. 12), thus establishing electrical and mechanical connections between the conductors and the connectors.

Weakened zone 170 preferably comprises the proximal ends of connectors 150 and 160, scored regions 156 and 166, blunt end 140, pins 151 and 161 and axial recess 157. Connectors 150 and 160 separate from needle 120 at scored regions 156 and 166 when a bending moment is applied to weakened zone 170.

Weakened zone 170 may be formed in ways that do not require connectors 150 and 160 to break in certain regions. For example, the amount of force applied when forming crimp 172 may be adjusted so that connectors 150 and 160 may be pulled out of blunt end 140 manually or when a special removal tool is used. Alternatively, pins 151 and 161 may have diameters sized to frictionally engage the inner sidewall of axial recess 157 with sufficient force to prevent their removal therefrom until a predetermined amount of outward force is applied to pull connectors 150 and 160 from blunt end 140.

FIGS. 7(a) through 7(d) show different views of a third preferred embodiment of the chest needle of the present invention. Connectors 150 and 160 are integral to and form the distal portion of electrically conductive, stainless steel needle 120. Notches 159 are machined in the top and bottom surfaces of connectors 150 and 160 to form weakened zone 170. Less preferably, weakened zone 170 consists of only one notch 159. The proximal ends of conductors 80 and 90 (not shown in FIGS. 7(a) through 7(d)) slide within recesses 155 and 165 and are preferably crimped in place, thus establishing electrical and mechanical connections between the conductors and the connectors. Connectors 150 and 160 separate from needle 120 at notches 159 when a bending moment is applied to weakened zone 170.

Figure 8:
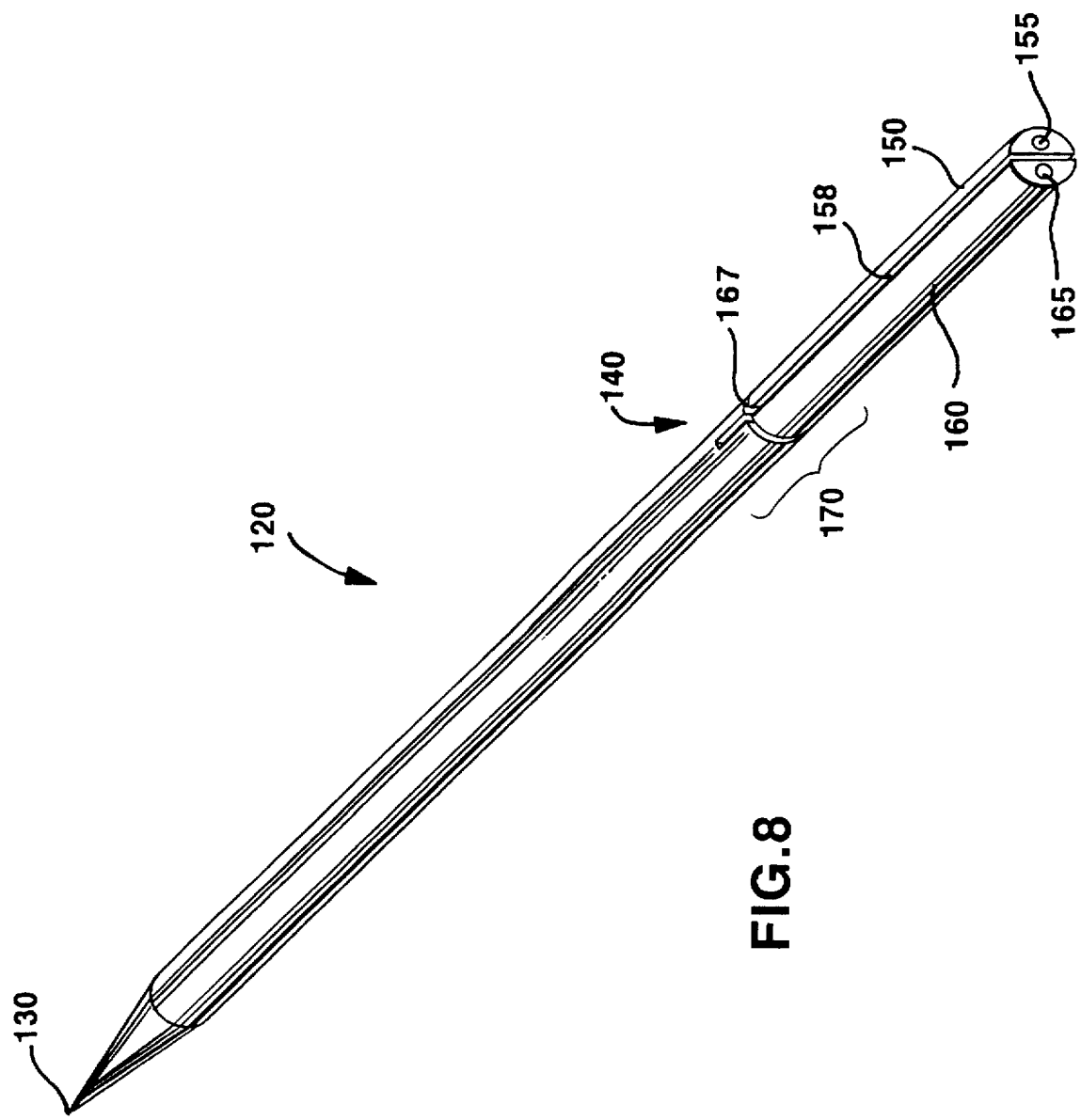
FIG. 8 shows a perspective view of a fourth preferred embodiment of the chest needle of the present invention.

FIG. 8 shows a perspective view of a fourth preferred embodiment of the chest needle of the present invention. Needle 120 and connectors 150 and 160 are machined, forged or otherwise formed of a single piece of stainless steel. Longitudinal groove 158 separates conductor 150 from conductor 160 along their respective entire lengths except near the intersection of blunt end 140, circumferential groove 167 and longitudinal groove 158, where conductors 150 and 160 are attached to blunt end 140 by a zone of reduced diameter stainless steel. Connectors 150 and 160 separate from needle 120 at circumferential groove 167 when a bending moment is applied to weakened zone 170.

Figure 9:
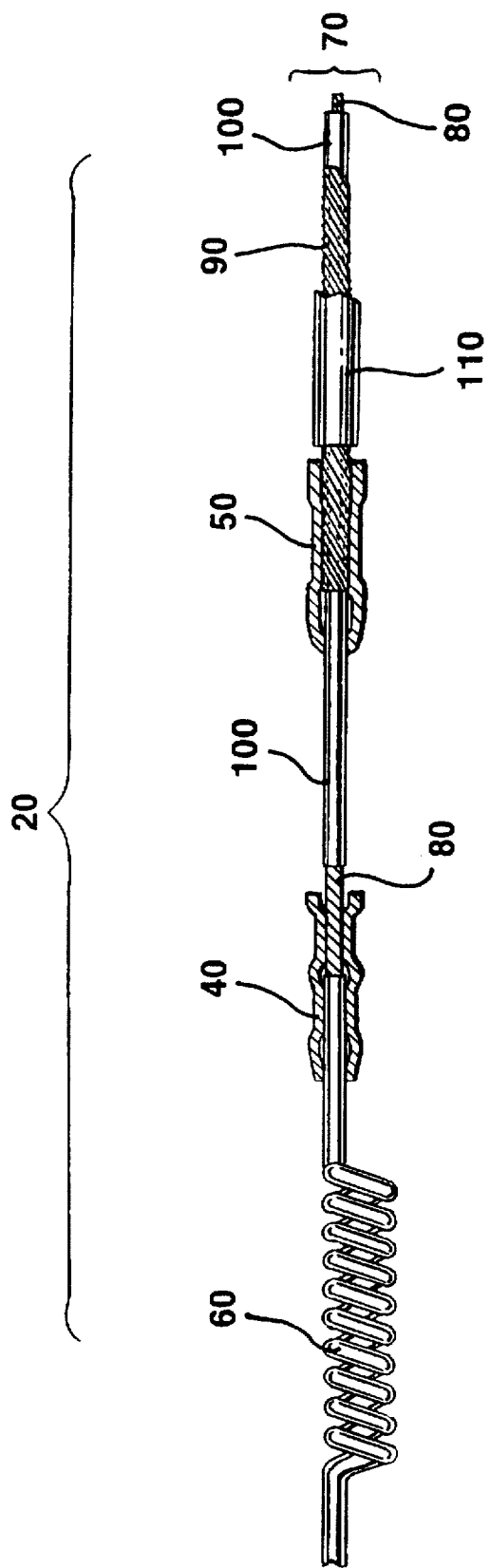
FIG. 9 shows an enlarged cross-sectional view of a portion of the distal end of a preferred embodiment of the present invention.

FIG. 9 shows an enlarged cross-sectional view of the distal end of one embodiment of the present invention, where lead 10 is designed specifically for pacing and sensing applications. FIG. 9 shows affixation coil 60 and electrodes 40 and 50 in greater detail. Affixation coil 60 preferably includes ten right hand wound turns and is crimpingly affixed to tip electrode 40. Inner conductor 80 is covered by inner insulation 100. Electrode 50 is crimpingly affixed to outer conductor 90 which is covered by outer insulation 110.

The two conductors of coaxial wire 70 preferably comprise twisted and helically wound strands of medical grade stainless steel wire. Less preferably those conductors may be formed of single strands of stainless steel, or of one or more strands of electrically conductive polymeric material. Inner insulation 100 is most preferably formed of fluorinated ethylene propylene (FEP), polytetrafluorethylene (PTFE), or any other suitable medical grade, biocompatible dielectric insulating coating such co-polymer polytetrafluorethylene, polyethylene, silastic, neoprene, polypropylene, or polyurethane. Inner insulation 100 covers and insulates inner conductor 80, which is preferably composed of 19 twisted, wound, or twisted and wound stainless steel filaments or strands.

Outer conductor 90 is preferably composed of 26 to 40 medical grade stainless steel strands or filaments, and most preferably 32 such strands, wound in helical fashion over inner insulation 80. Helical winding of the outer conductors imparts a high degree of flexibility to lead 10. Inner electrical insulation 100, disposed between the inner and outer electrical conductors, may be. Outer electrical insulation 110 is preferably formed of FEP or polyethylene, or any other suitable biocompatible material such as medical grade, biocompatible PTFE, polyethylene, silastic, neoprene, polypropylene, or polyurethane.

Figure 10:
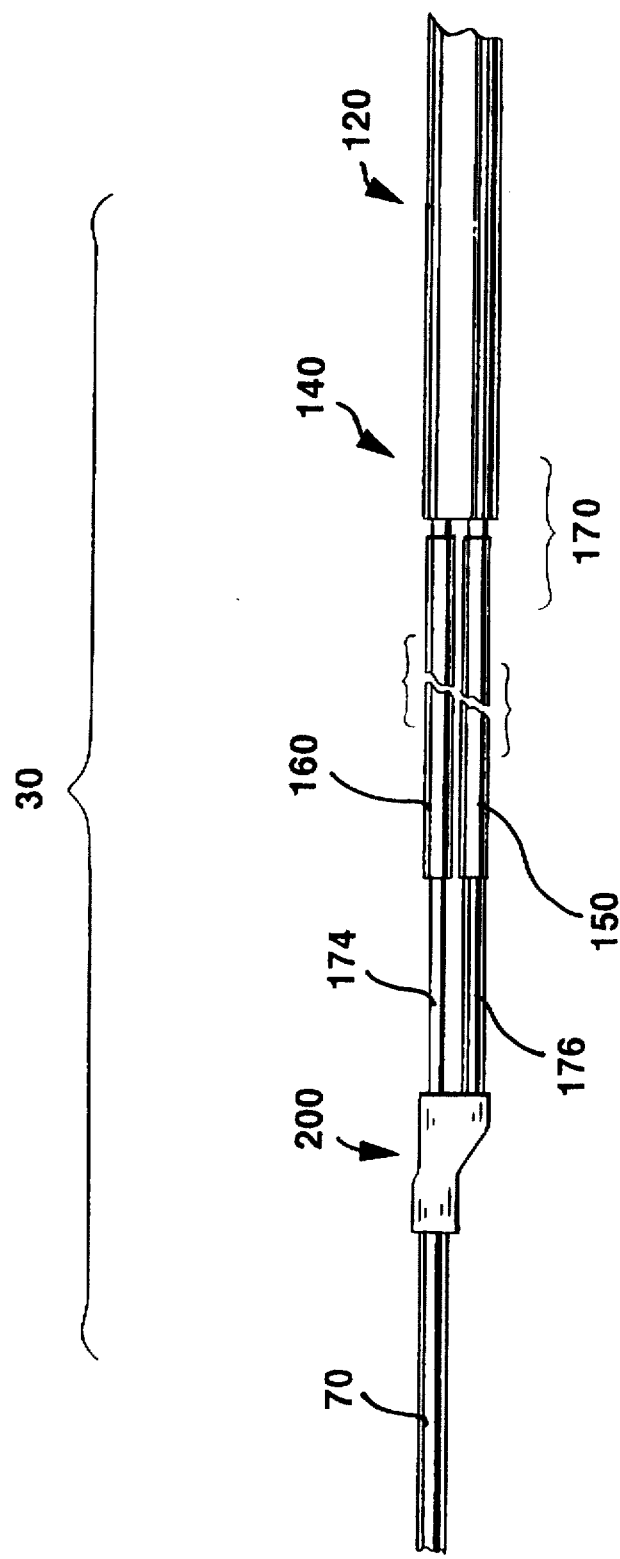
FIG. 10 shows an enlarged side view of a portion of the proximal end of a preferred embodiment of the present invention.

FIG. 10 shows an enlarged side view of a portion of the proximal end of a lead of the present invention, where two conductors and their corresponding layers of insulation are separated from one another at junction 200, most preferably formed of heat shrink tubing.

Figure 11:
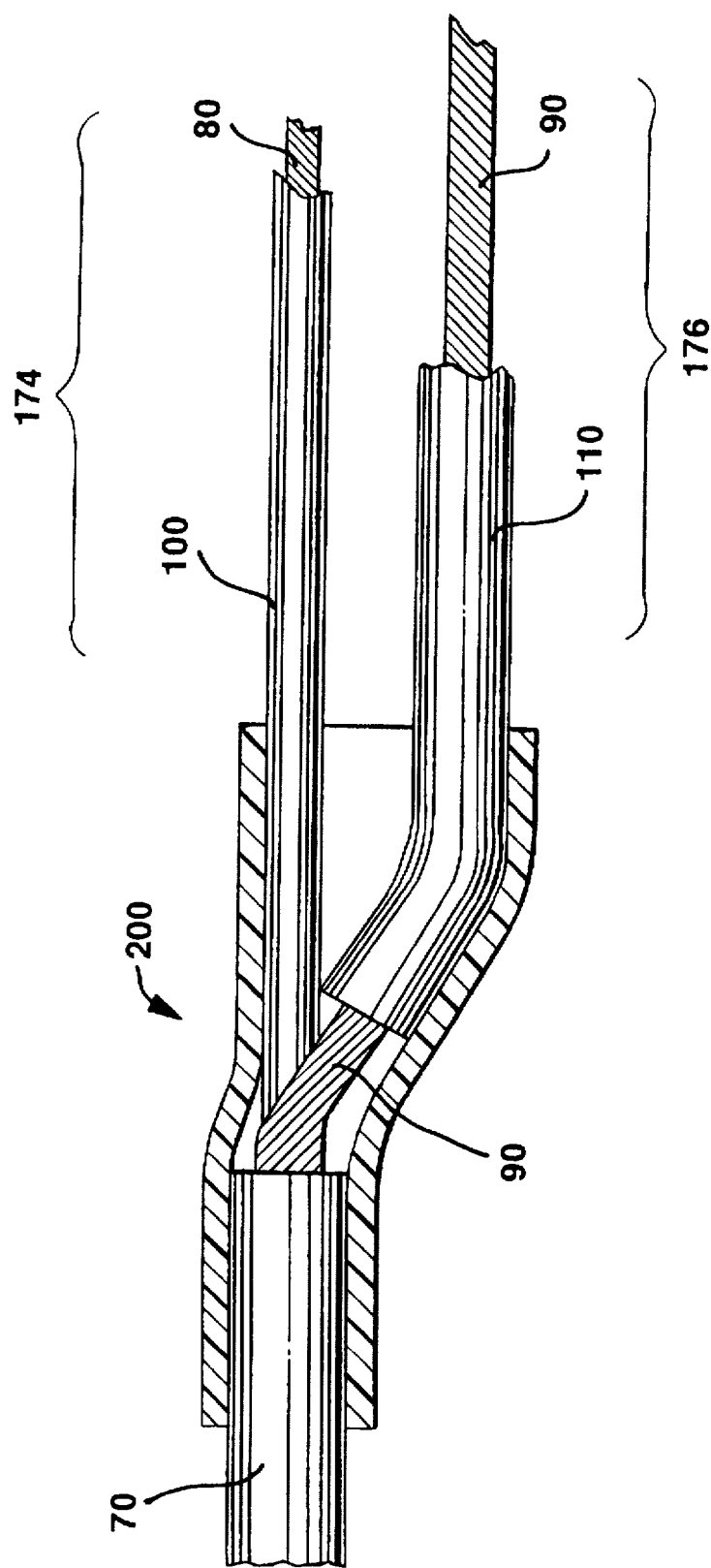
FIG. 11 shows an enlarged cross-sectional view of a portion of the proximal end of a preferred embodiment of the present invention.

FIG. 11 shows an enlarged cross-sectional view of junction 200, where coaxial conductor 70 is separated into two separate wires 174 and 176. First wire 174 comprises inner conductor 80 and inner insulation 100. Second wire 176 comprises outer conductor 90 and outer insulation layer 110.

Figure 12:
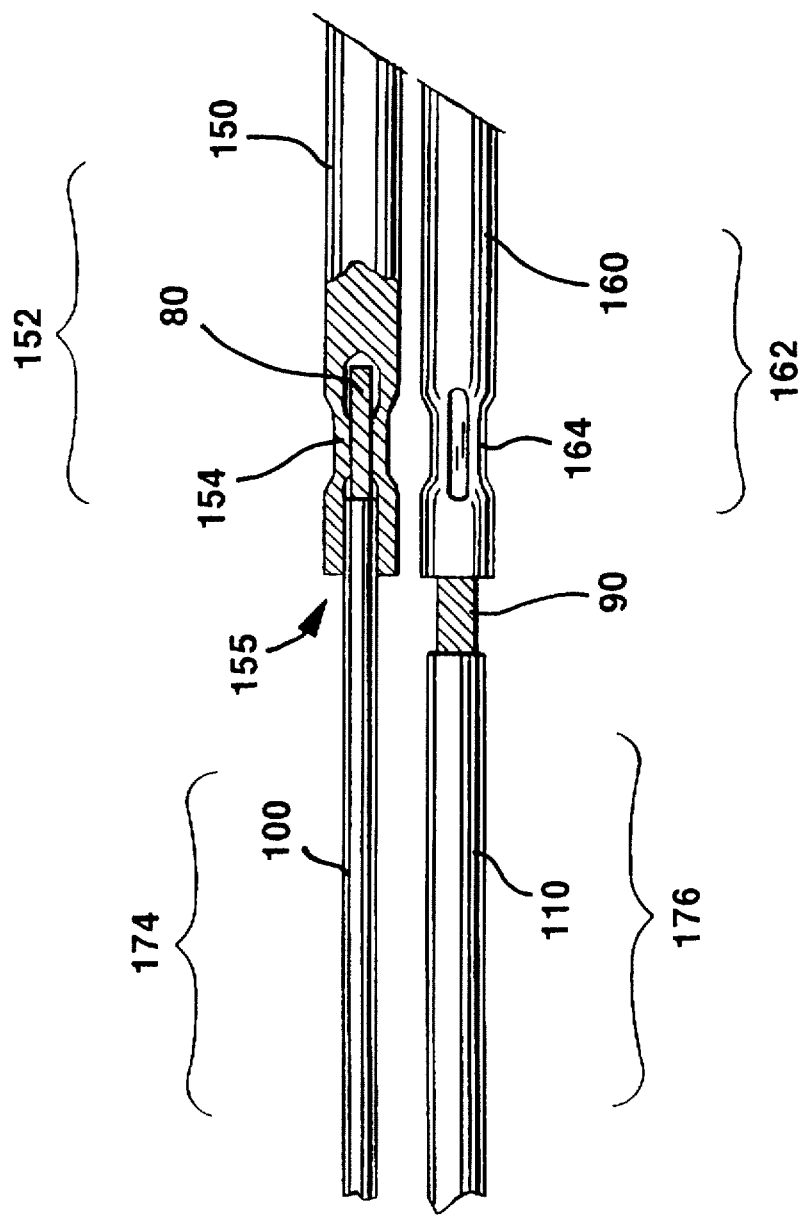
FIG. 12 shows an enlarged cross-sectional and side view of a portion of the proximal end of a preferred embodiment of the present invention.

At a distance proximal from junction 200 wires 174 and 176 are connected electrically and mechanically to connectors 150 and 160. As shown in FIG. 12, this is most preferably accomplished by stripping an appropriate length of overlying insulation away from the proximal ends of wires 174 and 176, compressing distal ends 152 and 162 of connectors 150 and 160 along vertical axes, inserting the bare wire ends into recesses 155 and 165, and crimping the wires in place to form crimps 154 and 164.

Figure 13:
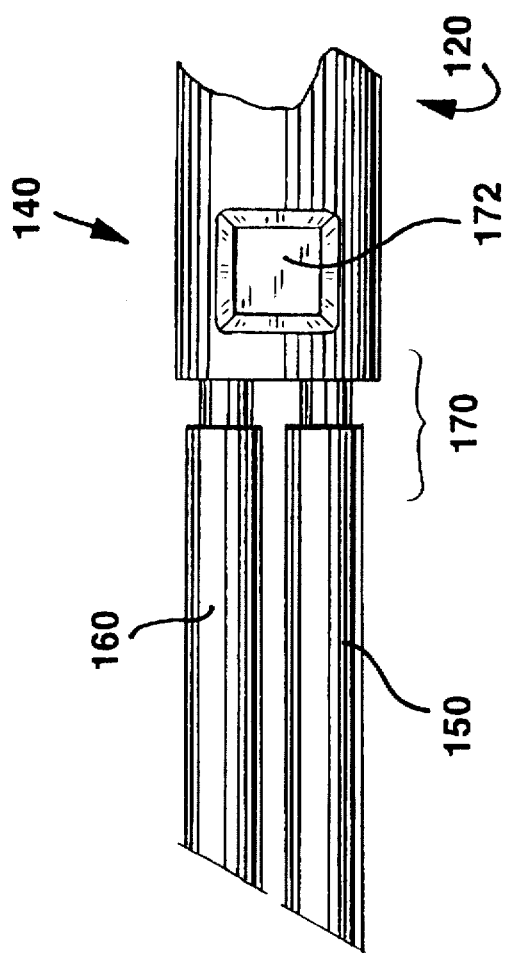
FIG. 13 shows an enlarged side view of a preferred embodiment of the weakened zone of the present invention.

FIG. 13 shows an enlarged side view of a preferred embodiment of weakened zone 170 of the present invention. Weakened zone 170 is shown being disposed between connectors 150 and 160 and needle 120. Crimp 172 compressionally holds pins 151 and 161 in blunt end 140 of needle 120.

The procedure for implanting lead 10 in the heart may be outlined briefly as follows. Fine curved needle 190 at distal end 20 of lead 10 is passed through the ventricular myocardium or epicardium. Affixation coil 60 and electrodes 40 and 50 are pulled through the heart tissue penetrated by needle 190 until the electrodes are located suitably within the myocardium or epicardium, and affixation coil 60 anchors electrodes 40 and 50 to the heart. Needle 190 and the portion of monofilament 180 extending from the heart are clipped off with a scissors, leaving the remainder of lead 10 extending from the heart. Chest needle 120 then pierces the patient's thorax, and is broken at weakened zone 170 to permit connectors 150 and 160 to be connected to an external sensing, monitoring, pacing or defibrillating device. When it is time to remove the lead, the surgeon simply carefully pulls the lead and withdraws it from the patient's heart and chest. Affixation coil 60 is flexible enough to allow the heart wire to be gently pulled from the myocardium or epicardium without damaging the myocardium.

Figure 14:
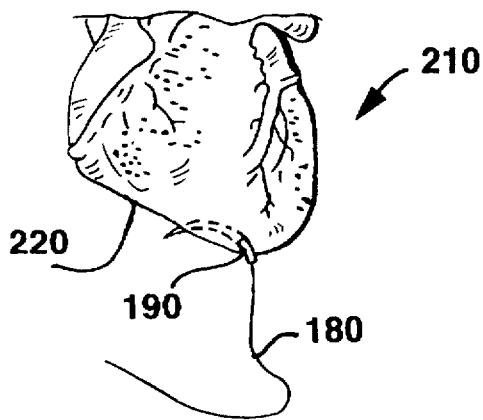
FIG. 14 shows a curved needle in a preferred embodiment of the present invention being inserted into the ventricular myocardium.

FIG. 14 shows curved needle 190 in a preferred embodiment of the present invention being inserted through epicardium 230 of ventricle 220 and into myocardium 240 of heart 210 preparatory to drawing bipolar lead 10 into myocardium 240 or epicardium 230.

Figure 15:
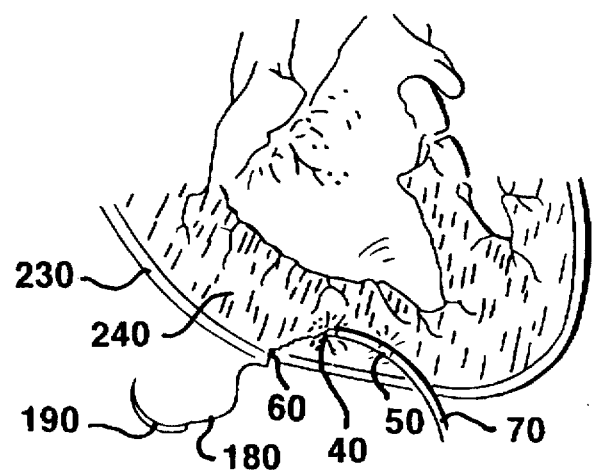
FIG. 15 shows a preferred embodiment of the present invention where both electrodes are positioned within the ventricular myocardium.
Figure 16:
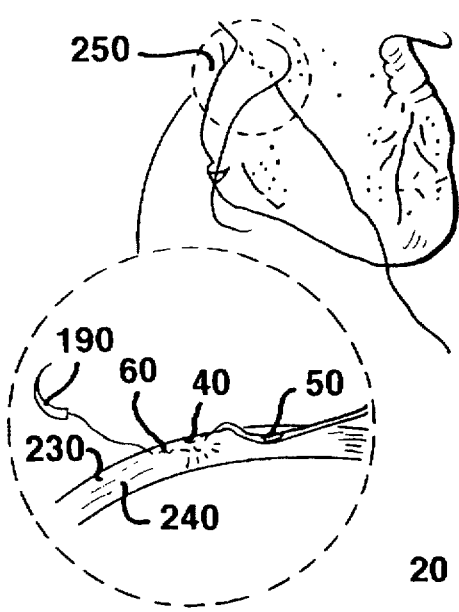
FIG. 16 shows a preferred embodiment of the present invention where the curved needle has pierced the atrial myocardium twice.

FIG. 15 shows a preferred embodiment of the present invention where electrodes 40 and 50 are positioned within ventricle 220 in myocardium 240 or epicardium 230. Affixation coil 60 prevents distal end 20 of lead 10 from FIG. 16 shows lead 10 positioned within myocardium 240 and epicardium 230 of atrium 250, where affixation coil 60 and electrodes 40 and 50 are positioned within myocardium 240 or epicardium 230. For atrial implantations the positioning of lead 10 shown in FIG. 16 may be preferred, where the surgeon pierces the atrium twice with curved needle 190, and a portion of lead 10 is positioned above heart 210. The lead positioning shown in FIG. 16 may be preferred as a means of preventing accidental penetration of the myocardium since the wall of atrium 250 is much thinner than that of ventricle 220.

Figure 17:
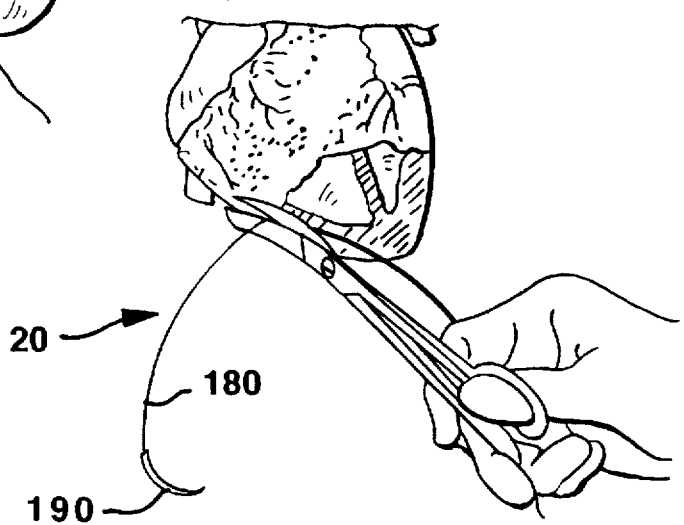
FIG. 17 shows removal of the curved needle from a heart wire of the present invention.

FIG. 17 shows the step in the implantation procedure where the surgeon cuts strand 180 at the exterior surface of the heart wall, leaving affixation coil 60 and electrodes 40 and 50 embedded in myocardium 240 or epicardium 230.

Although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

For example, the Figures show Keith-type needles, but any needle having suitably shaped and configured pointed and blunt ends and a suitable shank portion may be used. The needle need not be formed of stainless steel or an electrically conductive material, but may be formed of medical grade plastic, polymers or any other suitable material. Moreover, there is no requirement that the needle of the present invention be straight, substantially straight or solid in cross-section. Indeed, the needle of the present invention may be curved or hollow. Finally, the needle of the present invention need not have a pointed end because in some cases the needle may be withdrawn from a patient's body through an existing natural or surgically made orifice, hole or opening.

Since the connectors of the present invention are required to be in electrical contact with the conductors, the conductors are preferably attached to the distal ends of the connectors by a combination of compressing, inserting and crimping steps. Other methods of electrically conductive attachment such as brazing, soldering or welding may of course be utilized. The connectors of the present invention are not limited to pin connectors, but include any plurality of connectors having suitable configurations for attachment to the blunt end. The proximal ends of the connectors need not be removed from the needle by manual means only. Specially configured tools may be used to break or pull the connectors free of the needle.

The present invention is not limited to embodiments where the weakened zone breaks upon the application of sufficient bending moment thereto, or where the proximal ends of the connectors attach directly to the blunt end. The weakened zone may be formed of connectors whose distal ends attach gluingly, vaccuumingly, elastically or otherwise to the blunt end, or whose distal ends pull out of the blunt end upon sufficient pulling force being applied thereto. The weakened zone may further comprise an intermediate member disposed between the proximal ends of the connectors and the blunt end that may not be electrically conductive. For example, an intermediate member might be formed of plastic and be configured to break upon the application of an appropriate bending moment. The resulting separated connectors would then have non-conductive plastic portions disposed on their proximal ends, but those portions would not preclude effective electrical and mechanical connection between the connectors and an external electrical apparatus. Alternatively, the weakened zone might be formed, at least partially, of medical grade heat shrink tubing.

Furthermore, the present invention is not limited to embodiments where all electrodes are attached to the same lead body, where one electrode must necessarily be disposed proximally or distally of the other electrode or electrodes, or where the electrodes are crimpingly attached to the conductors. For example, an electrode of the present invention may be formed by merely stripping away insulation overlying bare wire at a suitable location, by attaching a clip to bare wire, or by heat shrinking electrically conductive heat shrink over selected portions of bare wire. Nor is the present invention limited to embodiments where the electrodes are introduced surgically with the aid of a curved needle through or into cardiac or other tissue. The present invention includes within its scope embodiments where the electrodes may be located on the surface of the heart, inside the atrium or ventricle, or on or in the endocardium.

The scope of the present invention is not limited to pacing, monitoring or sensing applications, but extends to neural, defibrillation, cardiac mapping, abdominal stimulation, and other medical and medical device applications and methods. The scope of the present invention is not limited to applications where a human organ or plurality of organs is sensed, monitored, paced, or defibrillated, but includes similar applications in animals.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The present invention further includes within its scope methods of implanting, using and making the leads described hereinabove. For example, the invention includes a method for implanting a temporary lead having distal and proximal ends, the lead being suitable for pacing, sensing, monitoring, or defibrillating at least a portion of a human or animal organ, the method comprising the steps of: (a) positioning at least two electrodes in electrical contact with the portion of the organ, the electrodes being electrically connected to first and second electrical conductors, respectively, the conductors having proximal ends connected electrically to first and second connectors, respectively, the connectors being configured for attachment to an external electrical apparatus; (b) securing the electrodes to the portion of the organ; and (c) separating the connectors from a blunt end of a chest needle having distal and proximal ends, the blunt end being disposed at the distal end of the needle, by application of a sufficiently large bending moment to a weakened zone disposed between the blunt end and the connectors. The foregoing method may optionally include the steps of: (a) a first piercing step that precedes the positioning step, the first piercing step comprising the step of piercing the organ with a pointed end of a curved needle, the curved needle being attached to the distal end of the lead, or (b) a second piercing preceding the separating step, the second piercing step comprising the step of piercing the thorax of a patient with a pointed end of the chest needle, the pointed end being disposed at the proximal end of the chest needle, or (c) a connecting step following the separating step, the connecting step comprising the step of electrically connecting the connectors to an external electrical apparatus. Alternatively, the separating step may be accomplished by application of a sufficiently large pulling force to the weakened zone such that the connectors are separated from the blunt end.

The present invention also includes within its scope a method for making a temporary lead having distal and proximal ends, where the lead is suitable for pacing, sensing, monitoring, or defibrillating at least a portion of a human or animal organ. The method of making comprises the steps of: (a) providing a lead body having distal and proximal ends and comprising at least first and second electrical conductors having proximal ends; (b) forming at least first and second electrodes, the first and second electrodes being electrically connected to the first and second electrical conductors, respectively; (c) providing a needle having distal and proximal ends, the needle having a blunt end disposed at its distal end; (d) providing first and second connectors; (e) attaching the first and second connectors to the proximal ends of the first and second electrical conductors, respectively; (f) providing a weakened zone between the first and second electrical connectors and the blunt end, the connectors being separated from the blunt end by application of a sufficiently large bending moment to the weakened zone, the connectors being configured for attachment to an external electrical apparatus. Alternatively, the separating step may be accomplished by application of a sufficiently large pulling force to the weakened zone.

We claim:

1. A temporary medical lead having distal and proximal ends, the lead being suitable for pacing, sensing, monitoring, or defibrillating at least a portion of a human or animal organ, comprising:

(a) a lead body having distal and proximal ends and comprising at least first and second electrical conductors having proximal ends, the first and second electrical conductors being electrically insulated from one another, and at least first and second electrodes attached, respectively, to the first and second electrical conductors, and (b) a substantially rigid needle assembly having distal and proximal ends, the needle assembly comprising: a first proximal portion comprising proximal and distal ends, the first portion having a pointed end disposed at the proximal end thereof, a second distal portion comprising at least first and second connectors having distal and proximal ends, the distal ends of the connectors forming the distal end of the needle assembly, the first proximal portion and the second distal portion being substantially rigidly connected to one another, a weakened zone being disposed at least propinguant to the region disposed between the first proximal portion and the second distal portion, the needle assembly, prior to the first and second portions thereof being manually separated from one another, forming a single contiguous and substantially rigid assembly, the first connector being attached to the proximal end of the first electrical conductor, the second connector being attached to the proximal end of the second electrical conductor;

wherein the connectors may be separated from the first proximal portion by the application of a single sufficiently large bending moment to the weakened zone, the connectors being configured for attachment to an external electrical apparatus.

2. The temporary lead of claim 1, wherein a strand having proximal and distal ends is attached to the distal end of the lead body.

3. The temporary lead of claim 2, wherein the strand is formed of polypropylene.

4. The temporary lead of claim 2, wherein the strand is a monofilament.

5. The temporary lead of claim 2, wherein the strand includes a coil affixation member.

6. The temporary lead of claim 5, wherein the coil affixation member includes ten right hand wound turns and is crimpingly affixed to one of the first and second electrodes.

7. The temporary lead of claim 2, wherein at least one atraumatic needle is attached to the distal end of the strand.

8. The temporary lead of claim 7, wherein the at least one atraumatic needle is curved.

9. The temporary lead of claim 1, wherein the distal ends of the at least first and second electrical conductors terminate in separate needles.

10. The temporary lead of claim 1, wherein the first and second conductors are formed of at least one of helically wound strands of multifilament stainless steel, twisted strands of multifilament stainless steel, single strands of stainless steel, and strands of electrically conductive polymeric material.

11. The temporary lead of claim 1, wherein the at least first and second electrical conductors are inner and outer coaxial conductors, respectively.

12. The temporary lead of claim 11, wherein a layer of inner insulation separates and electrically insulates the first inner conductor from the second outer conductor, the inner insulation being formed from a material selected from the group consisting of fluorinated ethylene propylene (FEP), polytetrafluorethylene (PTFE), co-polymer polytetrafluorethylene, polyethylene, silastic, neoprene, polypropylene and polyurethane.

13. The temporary lead of claim 12, wherein the outer conductor is composed of between about 26 and 40 medical grade stainless steel strands or filaments wound helically over the layer of inner insulation.

14. The temporary lead of claim 11, wherein a layer of outer insulation is disposed over the outer surface of the outer second conductor, the outer insulation being electrically insulative and formed from a material selected from the group consisting of FEP, polyethylene, biocompatible PTFE, polyethylene, silastic, neoprene, polypropylene and polyurethane.

15. The temporary lead of claim 11, wherein the inner conductor is composed of about 19 medical grade twisted, wound, or twisted and wound stainless steel filaments or strands .

16. The temporary lead of claim 12, wherein the outer conductor is composed of between about 26 and 40 medical grade stainless steel strands or filaments wound helically over the inner insulation.

17. The temporary lead of claim 1, wherein the at least first and second electrical conductors are zip cord conductors.

18. The temporary lead of claim 1, wherein the at least first and second electrodes are formed of medical grade stainless steel.

19. The temporary lead of claim 1, wherein the first electrode is a distal electrode, the first conductor forms an inner conductor, and the first electrode is mechanically and electrically connected by the inner conductor to the first connector.

20. The temporary lead of claim 1, wherein the second electrode is a proximal electrode, the second conductor forms an outer conductor, and the second electrode is mechanically and electrically connected by the outer conductor to the second connector.

21. The temporary lead of claim 1, wherein the first proximal portion of the needle assembly forms an atraumatic needle.

22. The temporary lead of claim 1, wherein the first portion of the needle assembly is substantially straight.

23. The temporary lead of claim 1, wherein the first portion of the needle assembly has a triangular cross-section.

24. The temporary lead of claim 1, wherein the first portion of the needle assembly is a Keith-type needle.

25. The temporary lead of claim 1, wherein the first portion of the needle assembly is formed of medical grade plastic or polymer.

26. The temporary lead of claim 1, wherein the first portion of the needle assembly is curved.

27. The temporary lead of claim 1, wherein the distal end of the first portion of the needle assembly is attached breakingly, snappingly, crimpingly, compressionally, frictionally, adhesively, gluingly, or elastically to the proximal ends of the first and second connectors.

28. The temporary lead of claim 1, wherein the first and second connectors, upon being separated from the first portion of the needle assembly, form cylindrically-shaped pin connectors having at least one of circular cross-sections, rectangular cross-sections and square cross-sections.

29. The temporary lead of claim 1, wherein the first and second connectors form reed-shaped connectors.

30. The temporary lead of claim 1, wherein the first and second connectors form flexible connectors.

31. The temporary lead of claim 1, wherein the first and second connectors have reduced diameter pins disposed at the proximal ends thereof.

32. The temporary lead of claim 31, wherein the first and second connectors each have a scored region disposed between the reduced diameter pin and its proximal end.

33. The temporary lead of claim 31, wherein the reduced diameter pins fit into corresponding individual recesses disposed within the distal end of the first portion of the needle assembly.

34. The temporary lead of claim 31, wherein the reduced diameter pins are frictionally engaged, adhered, glued, crimped, brazed, soldered or welded to the distal end of the first portion of the needle assembly.

35. The temporary lead of claim 1, wherein the proximal ends of the first and second conductors slide within recesses disposed in the distal ends of the first and second connectors, the conductors being crimped, brazed, soldered or welded in place therein to establish electrical and mechanical connections between the conductors and the connectors.

36. The temporary lead of claim 1, wherein the weakened zone is formed by crimping, scoring, machining or cutting a groove, a portion of a groove, or a notch on one or both sides of the connectors or the needle.

37. A temporary medical lead having distal and proximal ends, the lead being suitable for pacing, sensing, monitoring, or defibrillating at least a portion of a human or animal organ, comprising:
(a) a lead body having distal and proximal ends and comprising at least first and second electrical conductors having proximal ends, the first and second electrical conductors being electrically insulated from one another, and at least first and second electrodes attached, respectively, to the first and second electrical conductors, and
(b) a substantially rigid needle assembly having distal and proximal ends, the needle assembly comprising: a first proximal portion comprising proximal and distal ends, the first portion having a pointed end disposed at the proximal end thereof, a second distal portion comprising at least first and second connectors having distal and proximal ends, the distal ends of the connectors forming the distal end of the needle assembly, the first proximal portion and the second distal portion being substantially rigidly connected to one another, a weakened zone being disposed at least propinguant to the region disposed between the first proximal portion and the second distal portion, the needle assembly, prior to the first and second portions thereof being manually separated from one another, forming a single contiguous and substantially rigid assembly, the first connector being attached to the proximal end of the first electrical conductor, the second connector being attached to the proximal end of the second electrical conductor;
wherein the connectors may be separated from the first proximal portion by the application of a single sufficiently large pulling force to the weakened zone, the connectors being configured for attachment to an external electrical apparatus.

38. The temporary lead of claim 37, wherein a strand having proximal and distal ends is attached to the distal end of the lead body.

39. The temporary lead of claim 38, wherein the strand is formed of polypropylene.

40. The temporary lead of claim 38, wherein the strand is a monofilament.

41. The temporary lead of claim 38, wherein the strand includes a coil affixation member.

42. The temporary lead of claim 41, wherein the coil affixation member includes ten right hand wound turns and is crimpingly affixed to one of the first and second electrodes.

43. The temporary lead of claim 38, wherein at least one atraumatic needle is attached to the distal end of the strand.

44. The temporary lead of claim 43, wherein the at least one atraumatic needle is curved.

45. The temporary lead of claim 38, wherein the distal ends of the at least first and second electrical conductors terminate in separate needles.

46. The temporary lead of claim 38, wherein the first and second conductors are formed of at least one of helically wound strands of multifilament stainless steel, twisted strands of multifilament stainless steel, single strands of stainless steel, and strands of electrically conductive polymeric material.

47. The temporary lead of claim 38, wherein the at least first and second electrical conductors are inner and outer coaxial conductors, respectively.

48. The temporary lead of claim 47, wherein a layer of inner insulation separates and electrically insulates the first inner conductor from the second outer conductor, the inner insulation being formed from a material selected from the group consisting of fluorinated ethylene propylene (FEP), polytetrafluorethylene (PTFE), co-polymer polytetrafluorethylene, polyethylene, silastic, neoprene, polypropylene and polyurethane.

49. The temporary lead of claim 48, wherein the outer conductor is composed of between about 26 and 40 medical grade stainless steel strands or filaments wound helically over the layer of inner insulation.

50. The temporary lead of claim 47, wherein a layer of outer insulation is disposed over the outer surface of the outer second conductor, the outer insulation being electrically insulative and formed from a material selected from the group consisting of FEP, polyethylene, biocompatible PTFE, polyethylene, silastic, neoprene, polypropylene and polyurethane.

51. The temporary lead of claim 47, wherein the inner conductor is composed of about 19 medical grade twisted, wound, or twisted and wound stainless steel filaments or strands.

52. The temporary lead of claim 48, wherein the outer conductor is composed of between about 26 and 40 medical grade stainless steel strands or filaments wound helically over the inner insulation.

53. The temporary lead of claim 37, wherein the at least first and second electrical conductors are zip cord conductors.

54. The temporary lead of claim 37, wherein the at least first and second electrodes are formed of medical grade stainless steel.

55. The temporary lead of claim 37, wherein the first electrode is a distal electrode, the first conductor forms an inner conductor, and the first electrode is mechanically and electrically connected by the inner conductor to the first connector.

56. The temporary lead of claim 37, wherein the second electrode is a proximal electrode, the second conductor forms an outer conductor, and the second electrode is mechanically and electrically connected by the outer conductor to the second connector.

57. The temporary lead of claim 37, wherein the first proximal portion of the needle assembly forms an atraumatic needle.

58. The temporary lead of claim 37, wherein the first proximal portion of the needle assembly is substantially straight.

59. The temporary lead of claim 37, wherein the first proximal portion of the needle assembly has a triangular cross-section.

60. The temporary lead of claim 37, wherein the first proximal portion of the needle assembly is a Keith-type needle.

61. The temporary lead of claim 37, wherein the first proximal portion of the needle assembly is formed of medical grade plastic or polymer.

62. The temporary lead of claim 37, wherein the first proximal portion of the needle assembly is curved.

63. The temporary lead of claim 37, wherein the distal end of the first proximal portion of the needle assembly is attached crimpingly, compressionally, adhesively, gluingly, elastically, frictionally or slidingly to the proximal ends of the first and second connectors.

64. The temporary lead of claim 37, wherein the first and second connectors, upon being separated from the distal end of the first portion of the needle assembly, form cylindrically-shaped pin connectors having at least one of circular cross-sections, rectangular cross-sections and square cross sections.

65. The temporary lead of claim 37, wherein the first and second connectors form reed-shaped connectors.

66. The temporary lead of claim 37, wherein the first and second connectors form flexible connectors.

67. The temporary lead of claim 37, wherein the first and second connectors each have a reduced diameter pin disposed at its proximal end.

68. The temporary lead of claim 67, wherein the reduced diameter pins fit into corresponding axial recesses disposed within the distal end of the first portion of the needle assembly.

69. The temporary lead of claim 68, wherein the proximal ends of the connectors are frictionally engaged, adhered, glued, crimped, brazed, soldered or welded to the distal end of the first portion of the needle assembly.

70. The temporary lead of claim 37, wherein the first and second connectors have proximal ends that fit within corresponding axial recesses disposed within the distal end of the first portion of the needle assembly.

71. The temporary lead of claim 70, wherein the proximal ends of the first and second connectors are frictionally engaged, adhered, glued, crimped, brazed, soldered or welded to the distal end of the first portion of the needle assembly.

72. The temporary lead of claim 37, wherein the proximal ends of the first and second conductors slide within recesses disposed in the distal ends of the first and second connectors, the proximal ends of the conductors being crimped, brazed, soldered, or welded in place therein to establish electrical and mechanical connections between the conductors and the connectors.

73. The temporary lead of claim 37, wherein the weakened zone is formed by attaching elastically, frictionally engaging, crimping, gluing, brazing, soldering, or welding the proximal ends of the connectors to the distal end of the first portion of the needle assembly.

74. A temporary medical lead having distal and proximal ends, the lead being suitable for pacing, sensing, monitoring, or defibrillating at least a portion of a human or animal organ, comprising:

(a) a lead body having distal and proximal ends and comprising at least first and second means for conducting electricity, said first and second conducting means having proximal ends, the first and second electrical conductors being electrically insulated from one another, and at least first and second electrodes attached, respectively, to the first and second conducting means, and (b) a substantially rigid means for piercing assembly having distal and proximal ends, the piercing means assembly comprising: a first proximal portion comprising proximal and distal ends, the first portion having a pointed end disposed at the proximal end thereof, a second distal portion comprising at least first and second means for connecting having distal and proximal ends, the distal ends of the connecting means forming the distal end of the piercing means assembly, the first proximal portion and the second distal portion being substantially rigidly connected to one another, a means for weakening being disposed at least propinguant to the region disposed between the first proximal portion and the second distal portion, the piercing means assembly, prior to the first and second portions thereof being manually separated from one another, forming a single contiguous and substantially rigid assembly, the first means for connecting being attached to the proximal end of the first means for conducting, the second means for connecting being attached to the proximal end of the second means for conducting;

wherein the connecting means may be separated from the first proximal portion by the application of a sufficiently large bending moment to the weakening means, the connecting means being configured for attachment to an external electrical apparatus.

75. The temporary lead of claim 74, wherein a strand having proximal and distal ends is attached to the distal end of the lead body.

76. The temporary lead of claim 75, wherein the strand is formed of polypropylene.

77. The temporary lead of claim 75, wherein the strand is a monofilament.

78. The temporary lead of claim 75, wherein the strand includes a coil affixation member.

79. The temporary lead of claim 78, wherein the coil affixation member includes ten right hand wound turns and is crimpingly affixed to one of the first and second electrodes.

80. The temporary lead of claim 76, wherein at least one atraumatic needle is attached to the distal end of the strand.

81. The temporary lead of claim 80, wherein the at least one atraumatic needle is curved.

82. The temporary lead of claim 75, wherein the distal ends of the at least first and second conducting means terminate in separate needles.

83. The temporary lead of claim 75, wherein the first and second conducting means are formed of at least one of helically wound strands of multifilament stainless steel, twisted strands of multifilament stainless steel, single strands of stainless steel, and strands of electrically conductive polymeric material.

84. The temporary lead of claim 75, wherein the at least first and second conducting means are inner and outer coaxial conductors, respectively.

85. The temporary lead of claim 84, wherein a layer of inner insulation separates and electrically insulates the first inner conducting means from the second outer conducting means, the inner insulation being formed from a material selected from the group consisting of fluorinated ethylene propylene (FEP), polytetrafluorethylene (PTFE), co-polymer polytetrafluorethylene, polyethylene, silastic, neoprene, polypropylene and polyurethane.

86. The temporary lead of claim 84, wherein the outer conducting means is composed of between about 26 and 40 medical grade stainless steel strands or filaments wound helically over the layer of inner insulation.

87. The temporary lead of claim 84, wherein a layer of outer insulation is disposed over the outer surface of the outer second conducting means, the outer insulation being electrically insulative and formed from a material selected from the group consisting of FEP, polyethylene, biocompatible PTFE, polyethylene, silastic, neoprene, polypropylene and polyurethane.

88. The temporary lead of claim 84, wherein the inner conducting means is composed of about 19 medical grade twisted, wound, or twisted and wound stainless steel filaments or strands.

89. The temporary lead of claim 85, wherein the outer conducting means is composed of between about 26 and 40 medical grade stainless steel strands or filaments wound helically over the inner insulation.

90. The temporary lead of claim 75, wherein the at least first and second conducting means are zip cord conductors.

91. The temporary lead of claim 75, wherein the at least first and second electrodes are formed of medical grade stainless steel.

92. The temporary lead of claim 75, wherein the first electrode is a distal electrode, the first conducting means forms an inner conducting means, and the first electrode is mechanically and electrically connected by the inner conducting means to the first means for connecting.

93. The temporary lead of claim 75, wherein the second electrode is a proximal electrode, the second conducting means forms an outer conducting means, and the second electrode is mechanically and electrically connected by the outer conducting means to the second means for connecting.

94. The temporary lead of claim 75, wherein the first portion of the piercing means assembly is a needle.

95. The temporary lead of claim 94, wherein the first portion forms an atraumatic needle.

96. The temporary lead of claim 94, wherein the first portion of the piercing means assembly is substantially straight.

97. The temporary lead of claim 94, wherein the first portion of the piercing means assembly has a triangular cross-section.

98. The temporary lead of claim 94, wherein the first portion of the piercing means assembly is a Keith-type needle.

99. The temporary lead of claim 94, wherein the first portion of the piercing means assembly is formed of medical grade plastic or polymer.

100. The temporary lead of claim 94, wherein the first portion of the piercing means assembly is curved.

101. The temporary lead of claim 75, wherein the distal end of the first portion of the piercing means assembly is attached crimpingly, compressionally, adhesively, gluingly, elastically, frictionally or slidingly to the first and second means for connecting.

102. The temporary lead of claim 75, wherein the first and second means for connecting, upon being separated from the distal end of the first portion of the piercing means assembly, form cylindrically-shaped pin connectors having at least one of circular cross-sections, rectangular cross-sections and square cross-sections.

103. The temporary lead of claim 75, wherein the first and second means for connecting form reed-shaped connectors.

104. The temporary lead of claim 75, wherein the first and second means for connecting form flexible connectors.

105. The temporary lead of claim 75, wherein the first and second means for connecting each have a reduced diameter pin disposed at its proximal end.

106. The temporary lead of claim 105, wherein the reduced diameter pins fit into corresponding axial recesses disposed within the distal end of the first portion of the piercing means assembly.

107. The temporary lead of claim 106, wherein the proximal ends of the means for connecting are frictionally engaged, adhered, glued, crimped, brazed, soldered or welded to the distal end of the first portion of the piercing means assembly.

108. The temporary lead of claim 75, wherein the first and second means for connecting have proximal ends that fit within corresponding axial recesses disposed within the distal end of the first portion of the piercing means assembly.

109. The temporary lead of claim 108, wherein the proximal ends of the first and second means for connecting are frictionally engaged, adhered, glued, crimped, brazed, soldered or welded to the distal end of the first portion of the piercing means assembly.

110. The temporary lead of claim 75, wherein the proximal ends of the first and second means for conducting slide within recesses disposed in the distal ends of the first and second means for connecting, the means for conducting being crimped, brazed, soldered, or welded in place therein to establish electrical and mechanical connections between the means for conducting and the means for connecting.

111. The temporary lead of claim 75, wherein the means for weakening is formed by attaching elastically, frictionally engaging, crimping, gluing, brazing, soldering or welding the proximal ends of the means for connecting to the distal end of the first portion of the piercing means assembly.

112. A temporary medical lead having distal and proximal ends, the lead being suitable for pacing, sensing, monitoring, or defibrillating at least a portion of a human or animal organ, comprising:

(a) a lead body having distal and proximal ends and comprising at least first and second means for conducting electricity, said first and second conducting means having proximal ends, the first and second electrical conductors being electrically insulated from one another, and at least first and second electrodes attached, respectively, to the first and second conducting means, and (b) a substantially rigid means for piercing assembly having distal and proximal ends, the piercing means assembly comprising: a first proximal portion comprising proximal and distal ends, the first portion having a pointed end disposed at the proximal end thereof, a second distal portion comprising at least first and second means for connecting having distal and proximal ends, the distal ends of the connecting means forming the distal end of the piercing means assembly, the first proximal portion and the second distal portion being substantially rigidly connected to one another, a means for weakening being disposed at least propinguant to a region disposed between the first proximal portion and the second distal portion, the piercing means assembly, prior to the first and second portions thereof being manually separated from one another, forming a single contiguous and substantially rigid assembly, the first means for connecting being attached to the proximal end of the first means for conducting, the second means for connecting being attached to the proximal end of the second means for conducting;

wherein the connecting means may be separated from the first proximal portion by the application of a sufficiently pulling force to the weakening means, the connecting means being configured for attachment to an external electrical apparatus.

113. The temporary lead of claim 112, wherein a strand having proximal and distal ends is attached to the distal end of the lead body.

114. The temporary lead of claim 113, wherein the strand is formed of polypropylene.

115. The temporary lead of claim 113, wherein the strand is a monofilament.

116. The temporary lead of claim 113, wherein the strand includes a coil affixation member.

117. The temporary lead of claim 116, wherein the coil affixation member includes ten right hand wound turns and is crimpingly affixed to one of the first and second electrodes.

118. The temporary lead of claim 113, wherein at least one atraumatic needle is attached to the distal end of the strand.

119. The temporary lead of claim 118, wherein the at least one atraumatic needle is curved.

120. The temporary lead of claim 112, wherein the distal ends of the at least first and second conducting means terminate in separate needles.

121. The temporary lead of claim 112, wherein the first and second conducting means are formed of at least one of helically wound strands of multifilament stainless steel, twisted strands of multifilament stainless steel, single strands of stainless steel, and strands of electrically conductive polymeric material.

122. The temporary lead of claim 112, wherein the at least first and second conducting means are inner and outer coaxial conductors, respectively.

123. The temporary lead of claim 113, wherein a layer of inner insulation separates and electrically insulates the first inner conducting means from the second outer conducting means, the inner insulation being formed from a material selected from the group consisting of fluorinated ethylene propylene (FEP), polytetrafluorethylene (PTFE), co-polymer polytetrafluorethylene, polyethylene, silastic, neoprene, polypropylene and polyurethane.

124. The temporary lead of claim 123, wherein the outer conducting means is composed of between about 26 and 40 medical grade stainless steel strands or filaments wound helically over the layer of inner insulation.

125. The temporary lead of claim 122, wherein a layer of outer insulation is disposed over the outer surface of the outer second conducting means, the outer insulation being electrically insulative and formed from a material selected from the group consisting of FEP, polyethylene, biocompatible PTFE, polyethylene, silastic, neoprene, polypropylene and polyurethane.

126. The temporary lead of claim 122, wherein the inner conducting means is composed of about 19 medical grade twisted, wound, or twisted and wound stainless steel filaments or strands.

127. The temporary lead of claim 123, wherein the outer conducting means is composed of between about 26 and 40 medical grade stainless steel strands or filaments wound helically over the inner insulation.

128. The temporary lead of claim 112, wherein the at least first and second conducting means are zip cord conductors.

129. The temporary lead of claim 112, wherein the at least first and second electrodes are formed of medical grade stainless steel.

130. The temporary lead of claim 112, wherein the first electrode is a distal electrode, the first conducting means forms an inner conducting means, and the first electrode is mechanically and electrically connected by the inner conducting means to the first means for connecting.

131. The temporary lead of claim 112, wherein the second electrode is a proximal electrode, the second conducting means forms an outer conducting means, and the second electrode is mechanically and electrically connected by the outer conducting means to the second means for connecting.

132. The temporary lead of claim 112, wherein the first portion of the piercing means assembly is a needle.

133. The temporary lead of claim 132, wherein the needle is atraumatic.

134. The temporary lead of claim 132, wherein the needle is substantially straight.

135. The temporary lead of claim 132, wherein the needle has a triangular cross-section.

136. The temporary lead of claim 132, wherein the needle is a Keith-type needle.

137. The temporary lead of claim 132, wherein the needle is formed of medical grade plastic or polymer.

138. The temporary lead of claim 132, wherein the needle is curved.

139. The temporary lead of claim 112, wherein the distal end of the first portion of the piercing means assembly is attached crimpingly, compressionally, adhesively, gluingly, elastically, frictionally or slidingly to the proximal ends of the first and second means for connecting.

140. The temporary lead of claim 112, wherein the first and second means for connecting, upon being separated from the distal end of the first portion of the piercing means assembly, form cylindrically-shaped pin connectors having at least one of circular cross-sections, rectangular cross-sections and square cross-sections.

141. The temporary lead of claim 112, wherein the first and second means for connecting form reed-shaped connectors.

142. The temporary lead of claim 112, wherein the first and second means for connecting form flexible connectors.

143. A method for implanting a temporary medical lead having distal and proximal ends, the lead being suitable for pacing, sensing, monitoring, or defibrillating at least a portion of a human or animal organ, the lead comprising: (1) a lead body having distal and proximal ends and comprising at least first and second electrical conductors having proximal ends, the first and second electrical conductors being electrically insulated from one another, and at least first and second electrodes attached, respectively, to the first and second electrical conductors, and (2) a substantially rigid needle assembly having distal and proximal ends, the needle assembly comprising a first proximal portion comprising proximal and distal ends, the first portion having a pointed end disposed at the proximal end thereof, a second distal portion comprising at least first and second connectors having distal and proximal ends, the distal ends of the connectors forming the distal end of the needle assembly, the first proximal portion and the second distal portion being substantially rigidly connected to one another, a weakened zone being disposed at least propinquant to a region disposed between the first proximal portion and the second distal portion, the needle assembly, prior to the first and second portions thereof being manually separated from one another, forming a single contiguous and substantially rigid assembly, the first connector being attached to the proximal end of the first electrical conductor, the second connector being attached to the proximal end of the second electrical conductor, wherein the connectors may be separated from the first proximal portion by the application of a single sufficiently large bending moment or pulling force to the weakened zone, the connectors being configured for attachment to an external electrical apparatus, the method comprising the steps of:

(a) positioning the at least two electrodes in electrical contact with the portion of the organ;

(b) securing the electrodes to the portion of the organ, and (c) separating the connectors from the first portion of the needle assembly by the application of a sufficiently large bending moment or pulling force to the weakened zone.

144. The method of claim 143, wherein the positioning step is preceded by a first piercing step, the first piercing step comprising the step of piercing the organ with a pointed end of a curved needle, the curved needle being attached to the distal end of the lead.

145. The method of claim 143, wherein a second piercing step precedes the separating step, the second piercing step comprising the step of piercing the thorax of a patient with a pointed end of the chest needle, the pointed end being disposed at the proximal end of the chest needle.

146. The method of claim 143, wherein a connecting step follows the separating step, the connecting step comprising the step of electrically connecting the connectors to an external electrical apparatus.

147. A method for making a temporary medical lead having distal and proximal ends, the lead being suitable for pacing, sensing, monitoring, or defibrillating at least a portion of a human or animal organ, the lead comprising: (1) a lead body having distal and proximal ends and comprising at least first and second electrical conductors having proximal ends, the first and second electrical conductors being electrically insulated from one another, and at least first and second electrodes attached, respectively, to the first and second electrical conductors, and (2) a substantially rigid needle assembly having distal and proximal ends, the needle assembly comprising a first proximal portion comprising proximal and distal ends, the first portion having a pointed end disposed at the proximal end thereof, a second distal portion comprising at least first and second connectors having distal and proximal ends, the distal ends of the connectors forming the distal end of the needle assembly, the first proximal portion and the second distal portion being substantially rigidly connected to one another, a weakened zone being disposed at least propinquant to a region disposed between the first proximal portion and the second distal portion, the needle assembly, prior to the first and second portions thereof being manually separated from one another, forming a single contiguous and substantially rigid assembly, the first connector being attached to the proximal end of the first electrical conductor, the second connector being attached to the proximal end of the second electrical conductor, wherein the connectors may be separated from the first proximal portion by the application of a single sufficiently large bending moment or pulling force to the weakened zone, the connectors being configured for attachment to an external electrical apparatus, the method comprising the steps of:

(a) providing the lead body;

(b) providing the at least first and second electrodes;

(c) providing the needle assembly;

(d) attaching the distal ends of the first and second connectors to the proximal ends of the first and second electrical conductors, respectively;

(e) attaching the proximal ends of the first and second connectors to the distal end of the first portion of the needle assembly, and (f) providing the weakened zone.

148. A temporary medical lead having distal and proximal ends, the lead being suitable for pacing, sensing, monitoring, or defibrillating at least a portion of a human or animal organ, comprising:

(a) a lead body having distal and proximal ends and comprising at least first and second electrical conductors having proximal ends, the first and second electrical conductors being electrically insulated from one another, and at least first and second electrodes attached, respectively, to the first and second electrical conductors;

(b) a needle having distal and proximal ends, the needle having a blunt end disposed at its distal end;

(c) at least first and second connectors having proximal and distal ends, the first connector being attached to the proximal end of the first electrical conductor, the second connector being attached to the proximal end of the second electrical conductor, the first and second connectors having reduced diameter pins disposed at the proximal ends thereof, the reduced diameter pins fitting into corresponding individual recesses disposed within the blunt end, the reduced diameter pins being frictionally engaged, adhered, glued, crimped, brazed, soldered or welded to the blunt end, each of the first and second connectors having a scored region disposed between the reduced diameter pin and the proximal end thereof, the scored region forming a weakened zone, and (d) a weakened zone disposed between the first and second electrical connectors and the blunt end;

wherein the connectors may be separated from the blunt end by application of a sufficiently large bending moment to the weakened zone, the connectors being configured for attachment to an external electrical apparatus.

149. A temporary medical lead having distal and proximal ends, the lead being suitable for pacing, sensing, monitoring, or defibrillating at least a portion of a human or animal organ, comprising:

(a) a lead body having distal and proximal ends and comprising at least first and second electrical conductors having proximal ends, the first and second electrical conductors being electrically insulated from one another, and at least first and second electrodes attached, respectively, to the first and second electrical conductors;

(b) a needle having distal and proximal ends, the needle having a blunt end disposed at its distal end;

(c) at least first and second connectors, the first connector being attached to the proximal end of the first electrical conductor, the second connector being attached to the proximal end of the second electrical conductor, and (d) a weakened zone disposed between the first and second electrical connectors and the blunt end;

wherein the connectors may be separated from the blunt end by application of a sufficiently large pulling force to the weakened zone, the connectors being configured for attachment to an external electrical apparatus, the proximal ends of the first and second conductors sliding within corresponding recesses disposed in the distal ends of the first and second connectors, the proximal ends of the conductors being crimped, brazed, soldered, or welded in place therein to establish electrical and mechanical connections between the conductors and the connectors, the weakened zone being formed by attaching elastically, frictionally engaging, crimping, gluing, brazing, soldering, or welding the proximal ends of the connectors to the blunt end of the needle.

* * * * *

UNITED STATES PATENT AND TRADEMARK OFFICE
CERTIFICATE OF CORRECTION

PATENT NO. : 5,792,217
DATED : Aug. 11, 1998
INVENTOR(S) : Antione N. J. M. Camps et al.

It is certified that error appears in the above-indentified patent and that said Letters Patent is hereby corrected as shown below:

C. 16 L, 9     "at least propinguant" to be changed to "at least propinquant"
C. 18 L. 46    "at least propinguant" to be changed to "at least propinquant"
C. 21 L. 18    "at least propinguant" to be changed to "at least propinquant"

Signed and Sealed this

Ninth Day of November, 1999

Q. TODD DICKINSON

*Attest:*

*Attesting Officer*     Acting Commissioner of Patents and Trademarks